(12) United States Patent
Marci et al.

(10) Patent No.: US 10,198,713 B2
(45) Date of Patent: Feb. 5, 2019

(54) METHOD AND SYSTEM FOR PREDICTING AUDIENCE VIEWING BEHAVIOR

(71) Applicant: The Nielsen Company (US), LLC, New York, NY (US)

(72) Inventors: Carl D. Marci, Boston, MA (US); Brian Levine, Newton, MA (US); Ravi Kanth V Kothuri, Nashua, NH (US); Caleb J. Siefert, Boston, MA (US)

(73) Assignee: The Nielsen Company (US), LLC, New York, NY (US)

( * ) Notice: Subject to any disclaimer, the term of this patent is extended or adjusted under 35 U.S.C. 154(b) by 178 days.

(21) Appl. No.: 15/147,308

(22) Filed: May 5, 2016

(65) Prior Publication Data

US 2016/0255384 A1    Sep. 1, 2016

Related U.S. Application Data

(63) Continuation of application No. 12/749,376, filed on Mar. 29, 2010, now Pat. No. 9,514,436, which is a
(Continued)

(51) Int. Cl.
*G06Q 30/02* (2012.01)
*A61B 5/00* (2006.01)
(Continued)

(52) U.S. Cl.
CPC ......... *G06Q 10/10* (2013.01); *G06Q 30/0201* (2013.01); *H04N 21/252* (2013.01);
(Continued)

(58) Field of Classification Search
None
See application file for complete search history.

(56) References Cited

U.S. PATENT DOCUMENTS

| 4,859,050 A | 8/1989 | Borah et al. |
| 4,870,579 A | 9/1989 | Hey |

(Continued)

FOREIGN PATENT DOCUMENTS

| EP | 1503376 | 2/2005 |
| JP | 2001147944 | 5/2001 |

(Continued)

OTHER PUBLICATIONS

Wearable feedback systems for rehabilitation Sung, Michael; Marci, Carl; Pentland, Alex. Journal of Neuro Engineering and Rehabilitation 2 (2005), 2 pgs.*
(Continued)

*Primary Examiner* — Timothy Padot
(74) *Attorney, Agent, or Firm* — Hanley, Flight & Zimmerman, LLC

(57) ABSTRACT

The present invention is directed to a method and system for predicting the behavior of an audience based on the biologically based responses of the audience to a presentation that provides a sensory stimulating experience and determining a measure of the level and pattern of engagement of that audience to the presentation. In particular, the invention is directed to a method and system for predicting whether an audience is likely to view a presentation in its entirety. In addition, the present invention may be used to determine the point at which an audience is likely to change their attention to an alternative sensory stimulating experience including fast forwarding through recorded content, changing the channel or leaving the room when viewing live content, or otherwise redirecting their engagement from the sensory stimulating experience.

19 Claims, 11 Drawing Sheets

Related U.S. Application Data continuation-in-part of application No. 11/850,650, filed on Sep. 5, 2007, now Pat. No. 8,296,172.

(60) Provisional application No. 61/164,892, filed on Mar. 30, 2009, provisional application No. 60/824,546, filed on Sep. 5, 2006.

(51) Int. Cl.

| | | |
|---|---|---|
| *H04N 21/45* | (2011.01) | |
| *H04N 21/466* | (2011.01) | |
| *H04H 60/33* | (2008.01) | |
| *G06Q 10/10* | (2012.01) | |
| *H04N 21/25* | (2011.01) | |
| *H04N 21/258* | (2011.01) | |
| *H04N 21/422* | (2011.01) | |
| *H04N 21/84* | (2011.01) | |
| *A61B 5/024* | (2006.01) | |
| *A61B 5/053* | (2006.01) | |
| *A61B 5/11* | (2006.01) | |
| *A61B 5/22* | (2006.01) | |
| *A61B 5/08* | (2006.01) | |
| *A61B 5/0476* | (2006.01) | |
| *A61B 5/16* | (2006.01) | |

(52) U.S. Cl.
CPC . *H04N 21/25883* (2013.01); *H04N 21/42201* (2013.01); *H04N 21/4532* (2013.01); *H04N 21/4662* (2013.01); *H04N 21/84* (2013.01); *A61B 5/0002* (2013.01); *A61B 5/02405* (2013.01); *A61B 5/0476* (2013.01); *A61B 5/0533* (2013.01); *A61B 5/08* (2013.01); *A61B 5/11* (2013.01); *A61B 5/16* (2013.01); *A61B 5/225* (2013.01); *A61B 5/6897* (2013.01); *H04H 60/33* (2013.01)

(56) References Cited

U.S. PATENT DOCUMENTS

| | | | |
|---|---|---|---|
| 5,243,517 A | 9/1993 | Schmidt et al. | |
| 5,436,830 A | 7/1995 | Zaltman | |
| 5,676,138 A * | 10/1997 | Zawilinski | A61B 3/113 |
| | | | 128/905 |
| 5,676,148 A | 10/1997 | Koo et al. | |
| 5,842,199 A | 11/1998 | Miller et al. | |
| 6,099,319 A | 8/2000 | Zaltman et al. | |
| 6,292,688 B1 * | 9/2001 | Patton | A61B 5/04842 |
| | | | 600/300 |
| 6,315,569 B1 | 11/2001 | Zaltman | |
| 6,358,201 B1 | 3/2002 | Childre et al. | |
| 6,422,999 B1 * | 7/2002 | Hill | A61B 5/0488 |
| | | | 600/300 |
| 6,453,241 B1 | 9/2002 | Bassett, Jr. et al. | |
| 6,652,283 B1 * | 11/2003 | Van Schaack | G09B 5/00 |
| | | | 434/236 |
| 6,850,252 B1 | 2/2005 | Hoffberg | |
| 6,852,875 B2 | 2/2005 | Prakash | |
| 6,888,457 B2 | 5/2005 | Wilkinson et al. | |
| 7,797,186 B2 | 9/2010 | Dybus | |
| 7,930,199 B1 | 4/2011 | Hill | |
| 8,296,172 B2 | 10/2012 | Marci et al. | |
| 8,684,742 B2 | 4/2014 | Siefert | |
| 2001/0013009 A1 | 8/2001 | Greening et al. | |
| 2002/0002525 A1 * | 1/2002 | Arai | G06Q 30/02 |
| | | | 705/37 |
| 2002/0013717 A1 * | 1/2002 | Ando | A61B 5/0002 |
| | | | 705/4 |
| 2002/0059577 A1 | 5/2002 | Lu et al. | |
| 2003/0044021 A1 | 3/2003 | Wilkinson et al. | |
| 2003/0046683 A1 * | 3/2003 | Jutzi | H04N 7/17318 |
| | | | 725/2 |
| 2003/0063222 A1 | 4/2003 | Creed et al. | |
| 2003/0093792 A1 * | 5/2003 | Labeeb | H04N 7/163 |
| | | | 725/46 |
| 2003/0149344 A1 | 8/2003 | Nizan | |
| 2004/0088289 A1 * | 5/2004 | Xu | G06F 17/30787 |
| 2004/0133081 A1 | 7/2004 | Teller et al. | |
| 2004/0219184 A1 | 11/2004 | Brown et al. | |
| 2005/0060312 A1 | 3/2005 | Curtiss et al. | |
| 2005/0062637 A1 | 3/2005 | El Zabadani et al. | |
| 2005/0071462 A1 | 3/2005 | Bodin et al. | |
| 2005/0071865 A1 | 3/2005 | Martins | |
| 2006/0041548 A1 * | 2/2006 | Parsons | G06F 17/30873 |
| 2006/0129458 A1 | 6/2006 | Maggio | |
| 2007/0038516 A1 | 2/2007 | Apple et al. | |
| 2007/0066916 A1 | 3/2007 | Lemos | |
| 2007/0250901 A1 * | 10/2007 | McIntire | H04N 7/17318 |
| | | | 725/146 |
| 2008/0091512 A1 | 4/2008 | Marci et al. | |
| 2008/0097854 A1 * | 4/2008 | Young | G06Q 30/02 |
| | | | 705/14.43 |
| 2008/0147742 A1 | 6/2008 | Allen | |
| 2008/0221401 A1 | 9/2008 | Derchak et al. | |
| 2008/0222670 A1 * | 9/2008 | Lee | G09B 7/02 |
| | | | 725/10 |
| 2008/0255949 A1 | 10/2008 | Genco et al. | |
| 2009/0030780 A1 | 1/2009 | York et al. | |
| 2010/0004977 A1 | 7/2010 | Marci et al. | |
| 2010/0211439 A1 | 8/2010 | Marci et al. | |
| 2013/0046577 A1 | 2/2013 | Marci et al. | |

FOREIGN PATENT DOCUMENTS

| | | |
|---|---|---|
| JP | 2005051654 | 2/2005 |
| JP | 2006006355 | 1/2006 |
| JP | 2006227994 | 8/2006 |
| JP | 2007310454 | 11/2007 |
| WO | 9733515 | 9/1997 |
| WO | 2008030493 | 3/2008 |
| WO | 2008055078 | 5/2008 |
| WO | 2008072739 | 6/2008 |

OTHER PUBLICATIONS

One to One Interactive and Innerscope Research Release Preliminary Biomeasures Study Results. PR Newswire Feb. 28, 2007: NA.*

United States Patent and Trademark Office, "Final Office Action," issued in connection with U.S. Appl. No. 12/426,259, dated Jun. 19, 2017, 44 pages.

Von Leupoldt et al. "Emotions in a Body Plethysmograph," Journal of Psychophysiology 18 (4), 2004, 7 pages.

Hall, Bruce F., "A New Model for Measuring Advertising Effectiveness," Journal of Advertising Research, Mar.-Apr. 2002, 10 pages.

Marci et al., "The Effect of Emotional Distance on Pyschophysiologic Concordance and Perceived Empathy Between Patient and Interviewer", Applied Psychophysiology and Biofeedback, 31:115-129, 2006, 14 pages.

Miller et al., "Influence of Specific Emotional States on Autonomic Reactivity and Pulmonary Function in Asthmatic Children", J. Am. Acad. Child Adolescent Psychiatry, 36(5):669-677, May 1997, 9 pages.

United States Patent and Trademark Office, "Non-Final Office Actions," issued in connection with U.S. Appl. No. 12/426,259, dated Dec. 1, 2016, 52 pages.

European Patent Office, "Summons to attend oral proceedings pursuant to Rule 115(1)EPC," issued in connection with European Patent Application No. 07837771.0, dated Nov. 16, 2017, 9 pages.

Canadian Intellectual Property Office, "Office Action," issued in connection with Canadian patent application No. 2,758,272, dated Apr. 5, 2017, 4 pages.

Preliminary Opinion of the Examining Division, issued by the European Patent Office in connection with European Patent Application No. 10717932.7, dated Feb. 9, 2016, 11 pages.

(56) References Cited

OTHER PUBLICATIONS

Canadian Intellectual Property Office, "Office Action," issued in connection with Canadian Patent application 2,758,272 dated May 4, 2016, 5 pages.
Notice of Allowance and Fee(s) Due, issued by the United States Patent and Trademark Office in connection with U.S. Appl. No. 13/657,432, dated Apr. 25, 2016, 49 pages.
Final Rejection, issued by the United States Patent and Trademark Office in connection with U.S. Appl. No. 12/426,259, dated Sep. 24, 2015, 27 pages.
Horovitz, Bruce, "Watching Ads is Real Science Research Companies Monitor Physiological Reactions to Commercials to Determine Their Effectiveness," [3 Star Edition], Los Angeles Times, Orlando Sentinel, Sep. 1, 1991: D2, 2 pages.
Sung et al., "Wearable feedback systems for rehabilitation," Journal of NeuroEngineering and Rehabilitation 2, 2005, 2 pages.
First Examiner's Report, issued by IP Australia, in connection with corresponding Australian Patent Application No. 2007293092, dated Mar. 26, 2012, 2 pages.
First Examiner's Report, issued by IP Australia, in connection with corresponding Australian Patent Application No. 2013273825, dated Oct. 31, 2014, 2 pages.
European Patent Office "Communication Pursuant to Rules 161(2) and 162 EPC," issued in connection with European Patent Application 10717932.7, dated Nov. 29, 2011, 2 pages.
European Patent Office "Supplementary European Search Report," issued in connection with European Patent Application 10717932.7, dated Aug. 8, 2013, 14 pages.
European Patent Office, "European Examination Report," issued in connection with European Application No. 10 717 932.7, dated Jun. 26, 2015, 13 pages.
European Patent Office "Communication Pursuant to Rules 161(2) and 162 EPC," issued in connection with European Patent Application 10717912.9, dated Nov. 11, 2011, 2 pages.
International Search Report, issued by the International Searching Authority in connection with International patent application No. PCT/US2007/019398, dated Mar. 24, 2008, 1 page.
International Search Report, issued by the International Searching Authority in connection with International patent application No. PCT/US2010/031375, dated Nov. 9, 2010, 3 pages.
International Search Report, issued by the International Searching Authority in connection with International patent application No. PCT/US2011/033050, dated Nov. 22, 2011, 3 pages.
Notification of Reason(s) for Rejection, English version, issued by the Japanese Intellectual Property Office in connection with Japanese Patent Application No. JP2009527401, dated Apr. 25, 2012, 11 pages.
Notification of Reason(s) for Rejection, English version, issued by the Japanese Intellectual Property Office in connection with Japanese Patent Application No. JP2012505954, dated Dec. 4, 2013, 19 pages.
United States Patent and Trademark Office, "Non-Final Office Action," issued in connection with U.S. Appl. No. 11/850,650, dated Oct. 18, 2010, 9 pages.
United States Patent and Trademark Office, "Final Office Action," issued in connection with U.S. Appl. No. 11/850,650, dated Jun. 8, 2011, 11 pages.
United States Patent and Trademark Office, "Non-Final Office Action," issued in connection with U.S. Appl. No. 11/850,650, dated Dec. 13, 2011, 12 pages.
United States Patent and Trademark Office, "Notice of Allowance," issued in connection with U.S. Appl. No. 11/850,650, dated Jul. 16, 2012, 9 pages.
United States Patent and Trademark Office, "Restriction and/or Election Requirement," issued in connection with U.S. Appl. No. 12/426,259, dated Sep. 29, 2011, 8 pages.
United States Patent and Trademark Office, "Non-Final Office Action," issued in connection with U.S. Appl. No. 12/426,259, dated Apr. 25, 2012, 16 pages.
United States Patent and Trademark Office, "Non-Final Office Action," issued in connection with U.S. Appl. No. 12/426,259, dated Jan. 14, 2015, 26 pages.
United States Patent and Trademark Office, "Non-Final Office Action," issued in connection with U.S. Appl. No. 13/657,432, dated Feb. 21, 2013, 12 pages.
United States Patent and Trademark Office, "Final Office Action," issued in connection with U.S. Appl. No. 13/657,432, dated Nov. 5, 2013, 19 pages.
United States Patent and Trademark Office, "Non-Final Office Action," issued in connection with U.S. Appl. No. 13/657,432, dated Jul. 2, 2014, 11 pages.
United States Patent and Trademark Office, "Non-Final Office Action," issued in connection with U.S. Appl. No. 13/657,432, dated Aug. 5, 2014, 12 pages.
United States Patent and Trademark Office, "Final Office Action," issued in connection with U.S. Appl. No. 13/657,432, dated Feb. 24, 2015, 13 pages.
Canadian Office Action dated Jul. 24, 2014 of corresponding Canadian Patent Application No. 2,662,632, 3 Pages.
Supplementary Search Report dated Mar. 1, 2013, of corresponding European Patent Application No. 10717912.9, 2 pages.
United States Patent and Trademark Office, "Non-Final Office action," issued in connection with U.S. Appl. No. 12/749,376, dated Dec. 21, 2011, 40 pages.
European Office action dated Mar. 14, 2013 of corresponding European Patent application No. Application No. 10717912, 11 pages.
International Search Report dated Oct. 21, 2010 of corresponding International Patent Application No. PCT/US2010/029162, 12 Pages.
United States Patent and Trademark Office, "Non-Final Office action," issued in connection with U.S. Appl. No. 12/749,376, dated Oct. 4, 2012, 26 pages.
Boltz, M.G., "The cognitive processing of film and musical soundtracks", Memory & Cognition, 32(7): 1194-1205 (2004).
Christie et al., "Autonomic specificity of discrete emotion and dimensions of affective space: a multivariate approach", Int'l J Psychophysiol., 51:143-153 (2004).
Coombes et al., "Emotion and movement: Activation of defensive circuitry alters the magnitude of a sustained muscle contraction", Neurosci. Lett., 396:192-196 (2006).
Cryer et al., "Pull the plug on stress", Harv. Bus. Rev., 81(7):102-107 (2003).
United States Patent and Trademark Office, "Final Office action," issued in connection with U.S. Appl. No. 12/749,376, dated Apr. 1, 2013, 31 pages.
Ekman et al., "Autonomic Nervous System Activity Distinguishes among Emotions", Science, 221(4616):1208-1210 (1983), 5 pages.
Elton, C., "Measuring emotion at the symphony", http://www.boston.com, (2006), 3 Pages.
Goldberg, C., "Getting wired could help predict emotions", http://www.boston.com, pp. 1-4, Jun. 13, 2005.
Gomez et al., "Respiratory responses associated with affective processing of film stimuli", Bioi. Psychol. 68:223-235 (2005).
McCraty et al., "Electrophysiolocial Evidence ofIntuition: Part I. The Surprising Role ofthe Heart",J. Altern. Complement. Med., 10(1):133-143 (2004).
McCraty et al, "Electrophysiological evidence of intuition: Part 2. A system-wide process?", J. Altern. Complement. Med., 10(2/0):325-336 (2004).
McCraty et al, "Impact of a Workplace Stress Reduction Program on Blood Pressure and Emotional Health in Hypertensive Employees", J. Altern. Complement. Med., 9(3):355-369 (2003).
McCraty et al., "The Effects of Different Types of Music on Mood, Tension, and Mental Clarity", Altern. Ther. Health Me d., 4(1):75-84 (1998).
McCraty et al., "The Effects of Emotions on Short-Term Power Spectrum Analysis of Heart Rate Variability", Am. J. Cardiol., 76(14):1089-1093, Nov. 15, 1995.
McCraty et al., "The Impact of an Emotional Self-Management Skills Course on Psychosocial Functioning and Autonomic Recovery to Stress in Middle School Children", Integr. Physiol. Behav. Sci., 34(4):246-268 (1999).

(56) References Cited

OTHER PUBLICATIONS

Melillo, W., "Inside the consumer mind: What Neuroscience can tell us about marketing", httR:I/www.answerstream.com, (2006) 8 pages.
Murphy et al., "The Heart Reinnervates After Transplantation", Ann. Thorac. Surg., 69( 6): 1769-1781 (2000).
Umetani et al. "Twenty-Four Hour Time Domain Heart Rate Variability and Heart Rate: Relations to Age and Gender Over Nine Decades", J. Am. Coli. Cardiol, 31(3):593-601 (1998).
United States Patent and Trademark Office, "Notice of Allowance," issued in connection with U.S. Appl. No. 12/749,376, dated Jan. 29, 2016, 50 pages.
United States Patent and Trademark Office, "Final Office action," issued in connection with U.S. Appl. No. 12/749,376, dated Oct. 23, 2015, 28 pages.
United States Patent and Trademark Office, "Non-Final Office action," issued in connection with U.S. Appl. No. 12/749,376, dated Jul. 6, 2015, 24 pages.
United States Patent and Trademark Office, "Final Office action," issued in connection with U.S. Appl. No. 12/749,376, dated Mar. 13, 2015, 19 pages.
United States Patent and Trademark Office, "Non-Final Office action," issued in connection with U.S. Appl. No. 12/749,376, dated Aug. 29, 2014, 13 pages.
United States Patent and Trademark Office, "Final Office action," issued in connection with U.S. Appl. No. 12/749,376, dated Dec. 17, 2013, 37 pages.
United States Patent and Trademark Office, "Final Office action," issued in connection with U.S. Appl. No. 12/426,529, dated Dec. 19, 2012, 24 pages.
United States Patent and Trademark Office, "Notice of Allowance," issued in connection with U.S. Appl. No. 13/657,432, dated Jul. 29, 2016, 50 pages.
Indian Patent Office, "Examination Report", issued in connection with corresponding Indian patent application No. 946/KOLNP/2009, dated Sep. 9, 2016, 7 pages.
European Patent Office, "Result of Consultation", issued in connection with corresponding European Patent application 10717932, dated Jun. 15, 2016, 14 pages.
European Patent Office, "Communication Pursuant to Article 94 (3) EPC", issued in connection with corresponding European Patent application 07837771, dated Jul. 5, 2016, 7 pages.
Japanese Office Action dated Feb. 19, 2014 of corresponding Japanese Patent Application No. 2012-503596, 7 pages.
United States Patent and Trademark Office, "Notice of Allowability," issued in connection with U.S. Appl. No. 12/749,376, dated Aug. 3, 2016, 6 pages.
Hall, B.F., "Advertising as a factor of production", Admap, pp. 37-39 (2003).
Hall, B.F., "On Measuring the Power Communications", JAR, pp. 1-11 (2004).
Hall, B. F., "Research and strategy: a fall from grace", Admap, pp. 2-4 (2003).
Hall, B.F., "Review of Casting for Big Ideas, by Andrew Jaffe", pp. 1-2 (2003).
Hall, B. F., "Why Advertisers Do It", pp. 1-5 (2003).
Hubert et al., "Autonomic, neuroendocrine, and subjective responses to emotion-inducing film stimuli", Int'l J. Psychophysiol., 11:131-140 (1991).
Kallman, H. Effect of Blank Time on Picture Recognition. The American Journal of Psychology, vol. 97, No. 3, Autumn, 1984, pp. 399-406 [retrieved on Nov. 3, 2011]. Retrieved from the Internet: <URL: http://www.jstor.orgi'Qss/1422527.
"ARF, AAAA and ANA Are Getting Emotional about Engagement", Presentation, pp. 1-103 (2005).
Demaree et al., "Predicting facial valence to negative stimuli from resting RSA: Not a function of active emotion regulation", Cognition and Emotion, 20(2): 161-176 (2006).
Ranii, D., "Adding Science to Gut Check", The News & Observer, pp. 1 (2005).
Rosenberg, K., "Emotional R.O.I.", The Hub, pp. 24-25 (2006).
"Topline: Emotional Response to Advertising", MSW Research, pp. 1-6 (2005).
Hall, B.F., "A new Approach to Measuring Advertising Effectiveness," Article 1502a:1-17 (2001), 17 pages.
Hall, B.F., "Is cognitive processing the right dimension," Admap, pp. 37-39 (2003), 3 pages.
Levenson et al., "Emotion and Autonomic Nervous System Activity in the Minangkabau of West Sumatra," J. Personality Soc. Psychol., 62(6):972-988 (1992), 17 pages.
McCraty et al., "Analysis of twenty four hour heart rate variability in patients with panic disorder," Biol. Psychol., 56(2)131-150 (2001), 21 pages.
McCraty et al., "The Impact of New Emotional Self-Management Program on Stress, Emotions, Heart Rate Variability, DHEA and Cortisol," Intergr. Physiol. Behav. Sci., 32(2):151-170 (1998), 20 pages.
Tiller et al., "Cardiac Coherence a New, Noninvasive Measure of Autonomic Nervous System Order," Altern. Ther. Health Med., 2(1):52-65 (1996), 14 pages.
European Patent Office, "Decision to Refuse Patent Application and Minutes," issued in connection with corresponding European Patent application 10 717 932.7, dated Sep. 6, 2016, 33 pages.
United States Patent and Trademark Office, "Final Office action," issued in connection with U.S. Appl. No. 12/426,259, dated Dec. 19, 2012, 24 pages.
European Patent Office, "Decision of the Oral Proceedings", issued in connection with European application No. 078377710.0-1222, dated Jun. 8, 2018, 15 pages.
European Patent Office, "The Minutes in accordance with Rule 124(4)", issued in connection with European application No. 078377710.0-1222, dated Jun. 7, 2018, 9 pages.

\* cited by examiner

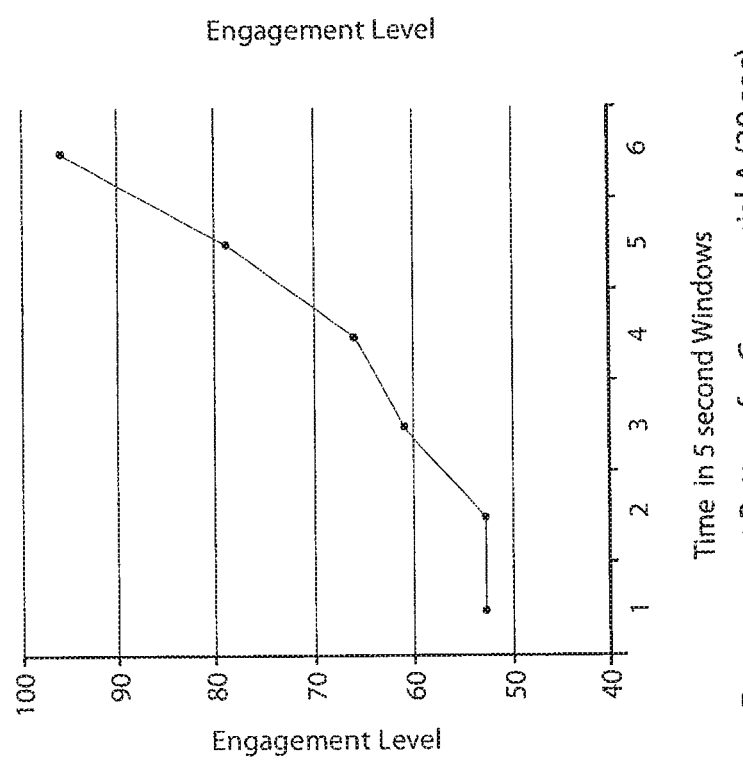

METHOD AND SYSTEM FOR PREDICTING AUDIENCE VIEWING BEHAVIOR

CROSS-REFERENCE TO RELATED APPLICATIONS

This patent arises from a continuation of U.S. application Ser. No. 12/749,376, titled "Method and System for Predicting Audience Viewing Behavior," and filed Mar. 29, 2010. U.S. application Ser. No. 12/749,376 is a continuation-in-part of U.S. application Ser. No. 11/850,650 (now U.S. Pat. No. 8,296,172), titled "Method and System for Determining Audience Response to a Sensory Stimulus." filed Sep. 5, 2007, which claims priority to U.S. Provisional Application No. 60/824,546, titled "Method and System for Determining Audience Response to a Sensory Stimulus." filed Sep. 5, 2006. U.S. application Ser. No. 12/749,376 also claims priority to U.S. Provisional Application No. 61/164,892, titled "Method and System for Predicting Audience Viewing Behavior of TV Networks," filed Mar. 30, 2009. U.S. application Ser. No. 12/749,376; U.S. application Ser. No. 11/850,650; U.S. Provisional Application No. 60/824,546; and U.S. Provisional Application No. 61/164,892 are incorporated herein by this reference in their entireties.

FIELD OF THE INVENTION

The present invention is directed to a method and system for predicting audience viewing behavior of media content including live and recorded presentations, commercials, and show segments on various platforms such as television, internet, and handheld devices. In particular, the method and system generally involves a) exposing a sample population audience to media content (the sensory stimulating experience), b) evaluating the audience's experience by measuring the biologically based responses of the audience to the media content and determining a measure of the level and pattern of intensity, synchrony and engagement of that audience to the media content, and c) predicting whether an audience member is likely to change their attention to an alternative sensory stimulating experience including fast forwarding through recorded content, changing the channel or leaving the room when viewing live content, or otherwise redirecting their engagement from the sensory stimulating experience.

BACKGROUND OF THE INVENTION

There are many different kinds of audio, visual and audio-visual presentations that people are exposed to every day. These presentations serve as sensory experiences that stimulate our senses and are known to result in biologically based responses that can be measured electronically and mechanically (for example, heart rate, respiration state, blood pressure, and skin conductance).

A commonly used approach in making measurements for evaluating these presentations is that of interrogation, wherein the television/media viewer and/or Internet user and/or game player is asked to identify himself or herself as a member of the television/media audience or as an Internet user or as a game player. In connection with television viewing, this inquiry is usually done by means of an electronic prompting and data input device (for example, as in a Portable People Meter by Arbitron, Inc.) associated with a monitored receiver in a statistically selected population and monitoring site. The member identification may also include age, sex, and other demographic data. It is common to store both the demographic data and the tuning data associated with each monitored receiver in the statistically selected monitoring site in store-and-forward equipment located within the monitoring site and to subsequently forward these data to a central office computer via a direct call over the public switched telephone network, or via the Internet, on a regular basis.

These non-biologically based self-report methods of measuring audience response are known to be highly error prone. Personal logs are subjective resulting in recall biases, home monitoring devices require event-recording by the person and suffer low compliance, while digital monitoring of cable and internet signals cannot identify which household member or members are in the audience nor can they evaluate the level of responsiveness by those members. In addition, self-report offers no ability to capture the biological responses to a media presentation. Thus, while methods of self-report offer valuable data, they are highly error prone and cannot track the moment-to-moment responses to media consumption.

Accordingly, a method and system of objectively monitoring audience's emotional reactions (engagement) to various forms and lengths of media would be advantageous. In addition, based on the technological advances in the realm of digital video recording, it would be beneficial to employ such a method and system in order to obtain an indication as to whether the intended audience will fast forward through a commercial if given the opportunity.

SUMMARY OF THE INVENTION

Historically, biologically based testing focuses on using one or two physiological responses (e.g., heart rate or electroencephaolography) to determining the specific emotion elicited in response to a particular stimulus, such as advertising media, be it a photograph, a print ad, or a television commercial. However, determining the specific emotion elicited does not help to predict how these emotional responses lead to desired behavioral responses or changes in behavior. Further, this testing focuses on the responses of individuals. Thus, it is desirable to identify physiologically or biologically based responses or patterns of responses in a population sample that can lead to or are associated with behavioral responses or changes in behaviors of the target population.

The present invention relates to a system and method for use in the field of audience measurement. Specifically, the invention is directed to a method and system for recording the biologically based audience responses to a presentation (for example, a live or recorded, passive or interactive audio, visual, audio-visual presentation) and for determining a measure of moment-to-moment and overall intensity, synchrony and engagement of the audience with that stimulus presentation. The measure of engagement of the sample population audience can then be used to estimate the level to which a population as a whole will be engaged by, or like or dislike, the same presentation. The measure of engagement of the audience when combined with eye-tracking technology can also be used to determine what elements of a presentation are most engaging relative to other elements in that or a similar presentation. The measures of intensity, synchrony and engagement can be used both for diagnostic value and/or to anticipate the success or failure of a presentation. This can be accomplished via predictive models for comparing, for example, the measure of intensity, synchrony or engagement of known successful presentations to the measure of engagement for an unknown or not previously evaluated presentation for a sample population (representative audience).

The invention can be used as a media testing tool used in place of or as a complement to traditional dial testing, self-report surveys and focus groups to measure audience reaction. The invention can utilize human neurobiology and embodied responses that are measured and processed in accordance with the invention to measure a sample audience reaction and predict the response of a more general audience.

In accordance with one embodiment, a sample audience of 2 or more people is presented with a piece of content (live or pre-recorded) that can last anywhere from 5 seconds to 5 hours (or more). The system according to the invention monitors the biometric responses of our viewers to obtain an objective measure of their response to said content.

Biometric response data can be gathered via a multi-sensor wearable body monitoring device that enables continuous collection of biologically based data that is time-stamped in order to correlate it to the presentation. This sensor package can include a measure of skin conductivity (SC), and can include any number of additional sensors to monitor responses such as heart response, brain waves, respiratory response, body movements, eye tracking, facial expressions and other biologically based signals.

The content that is presented to the audience as part of the presentation can include, but is not limited to, photographs, print advertisements, television programs, films, documentaries, commercials, infomercials, news reports, live content, live theater, theater recordings, mock trials, story boards, actor auditions, television pilots and film concepts, music, the Internet, gaming, etc.

In accordance with the invention, the response data can be collected individually, in a small group, or large group environment and be noninvasive (all sensors can be external).

In accordance with the invention, the system can track what presentation is being viewed, who is viewing the content and the biological response(s) of the audience members in time-locked correspondence to the viewed content or presentation. Thus, for a given piece of content or a presentation being viewed, the biological response of each member of the sample population can be associated with a portion of the content and the data from more than one sample audience gathered at different times and places can be combined. For the purposes of this invention, the sample audience (or sample population) can be a single individual who is monitored viewing the same content several times, such as over the course of several days.

In one embodiment, a system according to the invention can help content creators, distributors and marketers gain an objective view of how their audiences will respond to their content.

In one embodiment, the system can be used in a natural home environment and be as noninvasive as possible. The system can track what television (and other media) is being viewed by household members, which members are viewing and exactly which segments those members are watching.

To members of the household, they can control their media in the same way as before. For them, the main difference is that they must wear a sensor device (for example, a special article of clothing, a bracelet or other device) as they watch video or listen to music. In this example, this device can be used to determine how engaged they are with the media being played by using biological sensors. The system can make assessments about the data collected, for example, the greater the level of movement, the less likely the audience member is paying attention and the more likely they are engaged in a non-passive viewing experience.

In one embodiment, the data collected by the device is only used if the device or the viewer is determined to be close to the media display; otherwise, it is assumed the viewer is too far away from the media to experience it. The data is transmitted to the set-top box (STB) or receiver at regular intervals and associated with each audience members' identification plus information about the current media being consumed. This data can be packaged together in a database and served in real time.

In one embodiment of the system, to address compliance issues, users will not be able to change the channel unless they are wearing a functioning sensor device or charging a discharged unit in the outlet/dock attached to the STB or receiver.

This system according to the invention can be used by presentation and content creators to evaluate their programming before widely distributing it. For example, they can use the system to evaluate a sample audience by "pushing" the video and audio they want evaluated directly to a sample audience member's home entertainment systems or computer.

The present invention is directed toward a method for predicting viewership of a content stimulus. The content stimulus can take many forms including, but not limited to, show segments, presentations, commercials, and combinations thereof.

The method comprises a series of steps comprising: dividing the content stimulus into a preset number of intervals, obtaining an engagement score for each interval of the content stimulus based on the biometrics of an audience, using the engagement score to determine at least one metric, and predicting viewership based on the at least one metric.

In one embodiment, the metric may be negative buildup, positive buildup, average engagement score, maximum engagement score, and/or combinations thereof. In another embodiment, at least two metrics may be used to predict viewership.

According to one aspect of the invention, the engagement score is obtained by exposing the audience to the content stimulus over a period of time, wherein the period of time is divided into at least two intervals. Next, at least one biologically based response to the content stimulus for each member of the sample population is measured. The biologically based response may include at least one of heart rate, skin conductance, respiration state, motion, and eye tracking. An intensity value is determined as a function of at least one of the measured biologically based responses for each interval. A synchrony value is determined as a function of a rate of change of at least one of the measured biologically based responses for each interval. Finally, the engagement score is determined for each interval as a function of the intensity value and the synchrony value.

In one embodiment, the positive buildup may be determined by using the engagement scores for a content stimulus by: setting at least one threshold value, dividing the engagement curve into ascending segments defined by intervals that the engagement value remains relatively constant or increases, computing the area above the threshold value for each such ascending segment, summing the areas, and dividing the sum by the duration of the content.

According to another aspect of the invention, the negative buildup may be determined by using the engagement scores for a content stimulus by: setting at least one threshold value, dividing the engagement curve into descending segments defined by intervals that the engagement value remains relatively constant or decreases, computing the area below the threshold value for each such descending segment, summing the areas, and dividing the sum by the duration of the content.

In one embodiment, the viewership of the content stimulus may be predicted by using predetermined correlations between the metric and actual viewership data previously collected. In another embodiment, at least one metric may be used to predict whether a viewer will watch the entirety of the content stimulus when the content stimulus is previously recorded. In another embodiment, at least one metric may be used to predict whether a viewer will watch the entirety of the content stimulus when the content stimulus is presented live.

The present invention is also directed toward a computerized system for predicting viewership of a content stimulus. The system may include a plurality of sensors, each adapted for measuring a biologically based response to the content stimulus over a period of two or more time intervals. In addition, the system may include a computer processing system adapted for receiving data relating to the content stimulus and data from the plurality of sensors providing a measure of at least one biologically based response to the content stimulus. Further, the system may include an intensity processing module adapted for determining, for each time interval, at least one intensity value as a function of at least one of the measured biologically based responses. In addition, a synchrony processing module adapted for determining, for each time interval, at least one synchrony value as a function of at least one of the measured biologically based responses may be included. The system may also include an engagement processing module adapted for determining, for each time interval, at least one engagement value as a function of the at least one intensity value and the at least one synchrony value, and at least one metric selected from the groups consisting of negative buildup, positive buildup, average engagement score, and maximum engagement score.

In one embodiment, the system also includes a comparison module adapted for comparing at least one engagement value to an engagement value stored in a database corresponding to a second content stimulus, and an indicator adapted for indicating that the content stimulus is similar to the second content stimulus based on the comparison.

According to one aspect of the invention, the biologically based responses are chosen from the group consisting of heart rate, skin conductance, respiration state, motion, and eye tracking.

In one embodiment, the intensity processing module is adapted for determining the intensity value as a function of a standardized score. The standardized score is determined as a function of at least one of a peak value, a trough value, a median value, an average value and a rate of change value of at least one of the biologically based responses.

In one embodiment, the synchrony processing module is adapted for determining the synchrony value as a function of a variance of a rate of change value of at least one of the biologically based responses over at least a portion of the audience.

The present invention is also directed to a method of validating metrics associated with viewership of a content stimulus. The method includes: exposing the audience to the content stimulus over a period of time divided into at least two intervals, measuring at least one biologically based response to the content stimulus for each member of the sample population, determining at least one intensity value as a function of at least one of the measured biologically based responses for each interval, determining at least one synchrony value as a function of a rate of change of at least one of the measured biologically based responses for each interval, determining at least one engagement score for each interval as a function of at least one of the intensity values and at least one synchrony value, using the engagement score to determine engagement metrics comprising negative buildup, positive buildup, average engagement score, and maximum engagement score, normalizing the data, and determining correlations between the engagement metrics and commercially available viewership retention numbers.

According to one aspect of the invention the step of measuring at least one biologically based response comprises measuring at least one of heart rate, skin conductance, respiration rate, respiration state, motion, and eye tracking.

In one embodiment, the step of using the engagement score to determine engagement metrics comprises determining the negative buildup by: setting at least one threshold value, dividing the curve into descending segments defined by intervals that the engagement value remains constant or decreases, computing the area below the threshold value for each such ascending segment, summing the areas, and dividing the sum by the duration of the content.

In another embodiment, the step of using the engagement score to determine engagement metrics comprises determining the positive buildup by: setting at least one threshold value, dividing the curve into ascending segments defined by intervals that the engagement value remains constant or increases, computing the area above the threshold value for each such ascending segment, summing the areas, and dividing the sum by the duration of the content.

These and other capabilities of the invention, along with the invention itself, will be more fully understood after a review of the following figures, detailed description, and claims.

BRIEF DESCRIPTION OF THE FIGURES

Further features and advantages of the invention can be ascertained from the following detailed description that is provided in connection with the drawing(s) described below:

FIG. 4A shows an engagement pattern for a 30 second commercial according to the invention and FIG. 4B shows an engagement pattern for a 60 second commercial according to the invention.

DETAILED DESCRIPTION OF THE INVENTION

Figure 1:
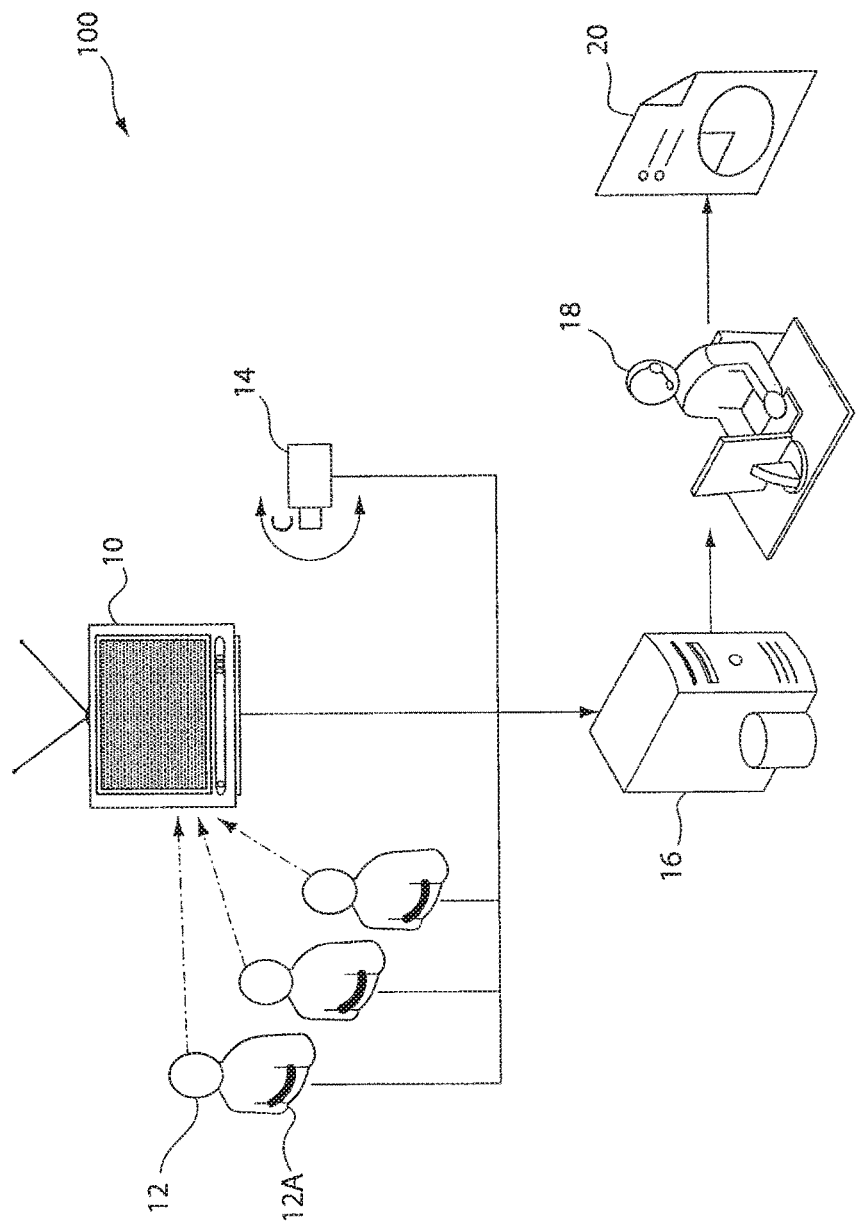
FIG. 1 is a schematic diagram of a system according to the invention for audience measurement in a test theater.

The present invention is directed to a method and system for determining a measure of a sample population's experience by measuring the biologically based responses of its members to a presentation that provides a sensory stimulating experience. Methods and systems according to the invention determine a measure of the level and pattern of intensity, synchrony and engagement of the sensory stimulating experience. In particular, the invention is directed to a method and system for measuring one or more biologically based responses of one or more persons being exposed to a sensory stimulus or presentation in order to determine the moment-to-moment pattern and overall level of engagement. Once the overall level of engagement is obtained, a prediction as to whether a person will act on an opportunity to bypass exposure (in part or whole) to the sensory stimulus can be provided. Furthermore, the invention can be used to determine whether the presentation is more effective with a population relative to other presentations and other populations and to help identify elements of the presentation that contribute to the high level of engagement and the effectiveness and success of the presentation.

There are many different kinds of audio, visual and audio-visual presentations that people are exposed to every day. These presentations serve as stimuli to our senses. Many of these presentations are designed to elicit responses. In some instances, an artist, musician or movie director has created a presentation that is intended to elicit one or more emotions or a series of responses from an audience. In other instances, the presentation is intended to educate or promote a product, a service, an organization, or a cause. Finally, there are often occasions and applications where the level of engagement of the audience is in response to a live person such as during a live performance, focus group, during an interview situation or any such social interaction.

These sensory stimuli can be in the form of a sound or a collection of sounds, a single picture or collection of pictures or an audio-visual presentation that is presented passively such as on television or radio, or presented in an interactive environment such as in a video game or internet experience. The sensory stimuli can be pre-recorded or presented live such as in a theatrical performance or legal proceeding (passive) or a real-world situation (or simulation) such as participating on a boat cruise or theme park ride (interactive).

Scientific research over the last two decades suggests that a person's responses to experiences are critical for the depth of processing of the content. The level of processing in turn affects the impact the content can have on the target audience and the ability to produce an attitudinal or behavioral change. Several studies even show that more arousing content leads to better recall of that content at a later date. This is of special interest to a variety of industry professionals including but not limited to creative directors, entertainment specialists, politicians and advertisers. For example, in the entertainment field, it is desirable to be able to assess which works are most appealing to which audiences (e.g., children, senior citizens, men and women).

Not only would this information be useful to the creator and the promoter in identifying the target audience, but also to corporate sponsors and advertisers for advertising purposes. The ability to estimate the overall impact of a given stimulus is also important to clinicians trying to educate patients, teachers inspiring students, or politicians persuading constituents. Thus, it is desirable to determine which, if any, demographic groups will find a particular piece of media content to be engaging in order to help determine its impact. Similarly, it is desirable to determine which, if any, demographic groups find a particular print, internet, television or radio commercial engaging in order to ultimately have the ability to predict human behavior, such as attitudinal change, purchasing activity, or social conduct.

Biologically based responses to passive and interactive presentations can be measured using various sensors affixed to the body to record various biological responses including but not limited to heart rate, respiration rate, motion, and skin conductivity. There are now multiple products and new technologies on the market that allow continuous unobtrusive monitoring of biologically based human responses, for example, many are often employed for health and fitness purposes. One product, offered under the name LifeShirt System (VivoMetrics, Ventura Calif.) is a state-of-the-art garment that is worn unobtrusively by a person being evaluated and can simultaneously collect pulmonary, cardiac, skin, posture and vocal information for later analysis. Another product, offered under the name SenseWear (BodyMedia, Pittsburgh Pa.) is an arm-band that simultaneously collects skin conductance, body temperature, motion, and heart rate. Also, a product offered under the name Tobii x50 Eye Tracker or Tobii 2150 (Tobii Technology, McLean Va.) is a state-of-the-art eye-tracking device that allows for unobtrusive monitoring of eye fixation location and fixation duration to a high degree of certainty. By combining eye-tracking with other biologically based responses, the system can uniquely predict what specific elements within a complex sensory experience (e.g., multimedia or Internet experience) are triggering the response.

In accordance with the invention, a method and system has been proposed that can reliably and objectively quantify moment-to-moment patterns and overall responses to passive and interactive audio, video, and audio-video content in a target audience as a whole. Rather than use individual biological responses to identify individual emotions in individual participants, the present invention is directed to methods and systems that can aggregate biologically based responses of a representative sample population of a target audience to create a moment-to-moment and overall index of engagement of the target audience with respect to a presentation that provides a sensory stimulating experience.

The present invention is directed to a method and system for collecting data representative of various biologically based responses of a person (or animal) to an audio, visual or audio-visual presentation that provides a sensory stimulating experience, such as a sound or sequence of sounds, a picture or a sequence of pictures including video, or a combination of one or more sounds and one or more pictures, including video. The presentation can be pre-recorded and played back on a presentation device or system (e.g., on a television, video display, projected on a screen, such as a movie) or experienced as a live performance. The presentation can be passive, where the audience experiences the presentation from a stationary location (e.g., seated in a theater or in front of a television or video screen) or the presentation can be interactive where the audience is participating in some form of activity (e.g., live roller coaster ride, simulated roller coaster ride, an interactive session via the internet, a focus group).

The data collected is processed in accordance with the invention in order to determine a measure of intensity, synchrony and engagement of the audience. The measure of intensity, synchrony and engagement for a population sample can further be used to predict the level of intensity, synchrony and engagement of the population. In the context of this disclosure, the population sample can be based on the measure of responses of a plurality of individuals to the same presentation (at the same time or different times) or multiple measures of responses of a single individual exposed to the same presentation multiple times.

In accordance with the present invention, a measure of the intensity of the response to the presentation over the period of exposure to the presentation and a measure of the synchrony of the response to the presentation over the period of exposure to the presentation can be determined from the biologically based responses. Further, the period of exposure can be divided into time slots or windows of a variety of durations (fixed or varying), or event based units with a corresponding response value determined for and associated with each time slot or event window. The measure of intensity can include measuring the change, from a base level, of a biologically based response to the presentation, aggregated across two or more biological measures and aggregated across the population or part of the population. Further, the response value can be determined as a function of the measured change and a set of predefined thresholds. The measure of synchrony can include determining a value indicative of the synchronized change or the correlation of the biologically based responses over the sample population. The measure of synchrony for a given time slot can be determined as a function of the inverse of the variance for the measured biologically based responses of the sample population for a common time slot. The measure of engagement can be determined by combining the measure of intensity and the measure of synchrony on a time slot by time slot basis. The measures of intensity and synchrony can be evenly or unevenly weighted in determining the measure of engagement.

The system can include three time-locked or synchronized sources of data: 1) a media presentation device or some other apparatus or forum for presenting the sensory stimulus or series of stimuli, 2) a response monitoring device for the collection of a plurality of biological responses to the presentation, and 3) an eye-tracking system and/or video camera to determine the location and duration of pupil fixation plus facial responses. Additional video cameras can be used to determine the proximity of the individual and/or audience to the media device and the specific elements of the presentation being experienced. The response monitoring device and the eye-tracking system and/or video camera can be time-locked or synchronized with the sensory stimulus so that the monitoring device and the eye-tracking system and/or video camera can consistently record the biological responses that correspond to the same portions of the presentation.

The system sensor package can include, but is not limited to, a measure of skin conductivity, heart rate, heart rate variability, vagal tone, respiration, body movement, measures of facial muscle movement/expression, eye-tracking and other biologically based signals such as body temperature, near body temperature, facial and body thermography imaging, facial EMG, EEG, fMRI and the like. The presentation content can include, but is not limited to, passive and interactive television, radio, movies, internet, gaming, and print entertainment and educational materials as well as live social interaction, theatrical, experiential, and amusement presentations. The time-locked data sources can be connected to or transferred to a computerized data processor to automatically apply the described method of scoring resulting in a pattern (or map) of engagement per unit time (time slot), per event, or across the entire presentation.

The system can further use eye-tracking, directional audio and/or video, or other technology to isolate specific elements or moments of interest for further in-depth processing. In accordance with the invention, the system can track what content is being viewed, who is viewing the content and which biological responses of the audience correspond to the viewed content.

The system can provide an objective view of how an audience will respond to a presentation. The system can further include a database of biologically based audience responses, response patterns and audience engagement patterns and levels to a variety of historic media stimuli that, when combined with demographic and other data relevant to the test media content, allows for a prediction of the relative success of that content.

A method is described for calculating an index of time-locked engagement. The method involves aggregation of the biological responses of the sample audience. In order to aggregate the responses of a sample population or group of participants, it is desirable to process the data according to one or more of the following procedures:

1. Time-locking the individual data streams into time slots or windows; the biological response data can be divided into sequential blocks that are associated with specific time slots;

2. Determining and processing the data based upon individual baselines and individual variances; the biological response data can be normalized to compensated for varying responses of the individual members of the sample population and the sensing equipment used;

3. Determining and processing the peak and trough values for each time slot to compare with the individual baselines and variances and determining and processing the rate of change for each time slot of one or more biological responses;

4. Determining a standardized score per time slot for each biological measure;

5. Combining the standardized score per time slot across the sample population using one or more of the standardized scores for one or more of the biological measures to create a measure of intensity. Preferably, more than one biological measure is used with at least one biological measure being weighted differently than other biological measures, depending on the sample population and presentation or content;

6. Averaging the inverse of the residual variance of the rate of change per unit time of a subset of biological measures across the test audience to create a measure of synchrony with some biological measures being weighted differently than other biological measures depending on the test population and test content;

7. Combining the measure of intensity and the measure of synchrony to create an overall measure of engagement per unit time. Preferably, either the measure of intensity or the measure of synchrony can be weighted differently, depending on the sample population and the presentation or content;

8. Standardizing the resulting measure of engagement per time slot to a set number of individuals (sample population size) for comparison with other tests in other populations of various sizes.

In accordance with one embodiment of the system, a sample audience is presented with a sensory stimulus or piece of media content (live or pre-recorded) in a test theater that can last from a minimum of a few seconds to several hours. For the purposes of this invention, the sample audience can be a single individual who is monitored viewing the same content several times or a group of individuals. Monitoring of audiences can be done individually, in small groups, or in large groups simultaneously. The audience can be of a tightly defined demographic/psychographic profile or from a broadly defined demographic/pyschographic profile or a combination of the two. The system records the time-locked data streams, calculates the level of moment-to-moment engagement, and compares the pattern of engagement to a database of similar media content. The system is further able to use eye-tracking or other technology to isolate specific elements or moments of interest for further in-depth processing. In accordance with the invention, the system can track what content is being viewed, who is viewing the content and which biological responses of the audience correspond to the viewed content. Thus, for a given piece of stimulus content, the biological responses can be connected with the portion of the content that elicited the response and the data from more than one sample audience or a subset of sample audiences gathered at different times and places can be aggregated.

In accordance with another embodiment, participating members of a household can control their media choice and usage throughout the course of their day while they wear a sensor device (for example, a special article of clothing, a bracelet or other device) that measures some, combination of biological responses as they watch television, listen to music, or use the internet. In this embodiment, the in-home sensing device communicates with an in-home computer or set top box (STB) that determines the nature and timing of the media content the participant has chosen as well as identifying information about the participant.

In this regard, the system would include a technology that could determine the distance from the media stimulus such as distance measurement via technologies like infrared, global positioning satellite, radar or through the acquisition of a signal between two objects, such as the television or computer and participant using technologies with a known range of operation (e.g., WiFi, Zigbee, RFID, or Bluetooth) and/or the direction of the participant eye-gaze (e.g., using eye-tracking technology). In a variant of this embodiment, the STB or computer can prevent activation of home media devices unless the sensor device was activated to ensure compliance. In another variant of this embodiment, test presentation content and/or broadcast/cable presentation content can be "pushed" to the participant that "matches" a desired demographic/psychographic profile or pre-determined level or pattern of engagement. As in prior embodiments, the system can record the time-locked data streams, calculate the moment-to-moment level of engagement relative to that person, and compare the pattern of engagement to a database of similar individual experiences.

In accordance with another embodiment, the presentation that provides that sensory stimulus can be a live person or persons or activity. This live person or persons may include, but is not limited to, live focus group interactions, live presentations to a jury during a pre-trial or mock-trial, an interview-interviewee interaction, a teacher to a student or group of students, a patient-doctor interaction, a dating interaction or some other social interaction. The live activity can be an activity, for example, riding on a rollercoaster, in a boat or in a car. The system can record the time-locked data streams, calculate the moment-to-moment level of engagement, and similar to the other embodiments, compare the pattern of engagement to a database of similar social interactions to make an estimate of the response pattern relative to other response patterns for that type of social interaction.

The present invention relates to a system and method for use in the field of audience measurement. A system is described for recording the biologically based audience responses to a live or recorded, passive or interactive audio, visual or audio-visual presentation that provides a sensory stimulating experience to members of the audience. A method is described for using the biologically based audience responses to calculate a pattern of intensity, synchrony and engagement measures. The method can involve the conversion of the biological responses of a plurality of participants into standardized scores per unit time, per event, or aggregated over time/events that can be aggregated across the sample population audience. The system determines the intensity and synchrony of the moment-to-moment and overall experience for the sample population audience. The standardized intensity and synchrony scores can be combined to create an overall measure of audience engagement. The measure of engagement represents an objective measure of the experience of a defined audience segment based on a plurality of biologically based measures.

The measure of engagement is determined from two components which are determined from the plurality of biologically based measures. The first component is the measure of intensity, which reflects the intensity of the biologically based responses to a plurality of defined portions of the presentation (represented by time slots or events). The second component is the measure of synchrony, which reflects the correlation or coincidence of the change in biologically based responses (how many people had the same or similar responses to the same content) in the sample population for a plurality of defined portions of the presentation (represented by time slots or events)

The system can further integrate time-locked eye-tracking and other video monitoring technology with the measure of engagement to identify specific elements of the sensory stimulus that are triggering the responses. The system can also use the measure of engagement to anticipate the relative success or failure of the test stimulus via predictive models using a database of historic patterns of engagement for similar test stimuli in similar audiences.

FIG. 1 shows a schematic diagram of an embodiment of the system according to the invention. The presentation is presented to the audience 12 via a display device 10, such as a video display screen or other commercially available technology for presenting the presentation to the test or sample audience 12. The presentation can include, but is not limited to, passive and interactive television, radio, movies, internet, gaming, and print entertainment and educational materials. The display device 10 can include but is not limited to a television, movie screen, a desk-top, hand-held or wearable computer device, gaming console, home or portable music device or any other device for the presentation of passive or interactive audio, visual or audio-visual presentation.

For the purposes of this invention, the test audience 12 can be a single individual who is monitored viewing the same content several times, or any small or large group defined by any number of parameters (e.g., demographics, level of interest, physiological or psychological profile). The test audience can be monitored using a biological monitoring system 12 a for the collection of a plurality of biological responses time-locked to each other and the test stimulus.

The system can include a focus and/or facial monitoring system 14 (e.g., eye-tracking system, or a digital video camera) for the collection of data on the behavior, facial response and/or precise focus of the audience. The three data-sources (media stimulus, biological response data, and focus data) can be synchronized or time-locked and/or event-locked to each other whereby the response data collected is associated with a portion of the presentation and sent to a computer data processing device 16. The computer data processing device can be a general purpose computer or personal computer with a processor, memory and software for processing the biological response data and generating the intensity, synchrony and engagement values.

The three data sources can be time-locked or synchronized externally or in the data processor 16 by a variety of means including but not limited to starting them all at the same time, or by providing a common event marker that allows the each system (in data processor 16) collecting the data from the three data sources to synchronize their clocks/event timers or simply synchronizing the clocks in each of the systems or use a common clock. The data processing device 16 can run software that includes the scoring algorithm to calculate the moment-to-moment, event-to-event or total level of engagement and compares it to a database of other audience responses to the same or similar test presentations and delivers the results to a user-interface 18. The user interface 18 can be provided on a desktop or portable computer or a computer terminal that accesses data processor 16. The user interface 16 can be a web based user interface or provided by a dedicated client running on the desktop or portable computer or computer terminal. The results can be interpreted and collected into a printed or electronic report 20 for distribution. The response data can be associated with the portion of the presentation that was displayed when the response was measured. Alternatively, the response data can be associated with an earlier portion of the presentation that is presumed to have caused the response based on a determined delay.

The monitoring device 12A for measuring biological responses can be any of a number of commercially available or other sensors known in the prior art for measuring such responses. In accordance with the current invention, the least invasive and obtrusive sensors with the most comfortable form factor should be chosen to minimize disruption of the experience. Preferably, the sensors should allow participants to experience the test stimulus "as if" they were not being monitored at all. Form factors include but are not limited to wearable devices such as smart garments, watches, and head-gear. Many devices are available and known to collect measures of the autonomic nervous system, facial musculature, motion and position, vocal features, eye-movements, respiratory states, and brain waves. Multiple combinations of sensors can be used depending on the sensory stimulus, population, and location of the monitoring.

An example of a method according to the invention for determining a measure of engagement can include obtaining any one or all of the following scores and employing predictive modeling.

Intensity Score

Each measure of intensity can be associated with point in time or a window or bin of time or event marker within the exposure period. This association can be accomplished using many methods. Preferably, the methodology for associating a measure of intensity with a point in time or a window of time within the exposure period is the same or similar for each measure of engagement determined in a population sample. For example, in one method, a given measure of intensity associated with a change in a biologically based response is assigned to the time slot or window that corresponds to where one half the rise time of that response occurs.

For example, the input to the data processor 16 can be an N by M data matrix where N is the number of subjects and M is the number of time points during which the biological response is recorded. The data processor 16 can include one or more software modules which receive the biological response data and generate the N by M matrix that is used in subsequent processing steps. The data processor 16 can include an intensity processing module which receives the N by M matrix of biological response data, calculates one or more standardized scores for each biological response measured and each time slot. The output can be a total integer score of the intensity of response across subjects in time windows of W seconds width (this is a variable parameter that depends on the presentation). The fractional rise time parameter (f-rise) can be used to estimate the related time window or slot in which the response occurs. For example, if a change in a biologically based response occurs over three time slots or windows, W1, W2, W3, and one half the rise-time of the response occurred during window W2, the measure of intensity for the change in response would be associated with window W2. Alternatively, the measure of intensity could be associated with the window that contained the peak (i.e., window W3) or the window that contained the trough (i.e., window W1). In addition, a fractional standard deviation parameter (f-std) can be used to estimate the degree of the change in response from baseline.

As a result, for each person, a response map can be determined as a set of intensity values associated with each time (or event) window during which each person was exposed to the presentation. The measure of intensity for the sample population can be determined by adding the measure of intensity associated with the same time window for each person exposed to the presentation. The result is a response time line that is the aggregate of the population sample. The response patterns for two or more biologically based responses (e.g., skin conductivity, heart rate, respiration rate, motion, etc.) can be combined (evenly or unevenly weighted) in a time window by time window basis to determine an overall intensity score or intensity time line. The aggregate can be normalized for a population size, for example 10 or 25 people.

In accordance with the invention, the response map or pattern can be used to evaluate radio, print and audio-visual advertisements (for both television and the Internet), television shows and movies. In one embodiment, a population sample can be exposed to one or more known successful advertisements (TV shows, movies, or websites) and then the same or a different population sample can be exposed to a new advertisement (TV show, movie, or website). Where the response pattern is similar to the response pattern to one or more known successful advertisements (TV shows, movies, or websites) it would be expected that the new advertisement (TV show, movie, or website) would also be successful. Further, a database of response patterns for different types of stimuli (advertisements, TV shows, movies, websites, etc.) could be maintained and analyzed to determine the attributes of a successful advertisement. TV show, movie, or website.

In accordance with the invention, the data processor 16 can include a synchrony processing module which receives the N by M matrix of biological response data, calculates the in verse variance of the rate of change of one or more biological measures across at least a portion of the sample population and determines a standardized value representative of the synchrony for a given time slot. The data processor 16 can determine the synchrony of a given biological response by evaluating the slope of the response in a given time window or event window over the period of exposure for each person in the population sample. For each time window, a slope value can be assigned based on the value of the slope, for example, the greater the slope the greater the slope value. The slope value for each corresponding time window or event window of each person of the population sample can be processed to determine a measure of the variance over the population sample for each time window or event window. For example, the mean and standard deviation of the slope value of the population sample for each time window or event window can be determined and used to further determine the residual variance. The residual variance can be further normalized and used to produce a response pattern that indicates the time-locked synchrony of the response of the population sample to the stimulus.

Similarly, the synchrony response map or pattern can be used to evaluate radio, print and audio-visual advertisements (for both television and the Internet), television shows and movies. Further, the stimuli described can be evaluated using both the intensity response pattern and the synchrony response pattern.

The intensity score can be calculated according to the following steps

Step 1: Following a noise reduction process for each input channel, for each participant, the distribution of amplitudes of responses including the mean ($\mu$) and standard deviation ($\sigma$) of responses is calculated over some baseline period (this is a variable parameter that depends on the stimulus).

Step 2: For each participant, the location and timing of the trough and peak amplitude of each response is estimated and the difference between each peak and trough (the amplitude of response) is calculated.

Step 3: The values so determined are used to establish a score for each individual response thus: score 0 if the amplitude is less than the baseline $\mu$ for that channel, score 1 for a response if the amplitude is between $\mu$ and $\mu+f-(\sigma)$, and score 2 for a response if the amplitude is greater than $\mu+f-(\sigma)$.

Step 4: Each response score for each participant is assigned to a sequential bin of variable length time-locked to the media stimulus by locating the time of the f-rise.

Step 5: The sum of all the binned response scores across all participants is calculated for each biological sensor. The score is normalized depending on the number of sensors collected (being equal for each test) and the number of participants (being unequal for each test). The score thus created is the intensity score per unit time or per time slot.

Depending on the sensors used and the presentation being experienced, not all channels will be added to the intensity score. For example, certain forms of respiration (such as a sigh indicative of boredom) or motion (taking a drink or looking at a watch) may actually be subtracted from the intensity score. In addition, alternative versions of the intensity measure may be used for presentations with differing goals. For example, when testing a horror movie, sensors such as skin conductance may be weighted more heavily in the calculation because the goal of the content is to generate arousal while testing a comedy, which is meant to elicit laughter, might use stronger weighting towards the respiratory response.

Additional methods of determining intensity score are disclosed in U.S. patent application Ser. No. 12/426,259, which is hereby incorporated by reference in its entirety.

Synchrony Score

Synchrony is a measure of the rate of change of a response by the audience (plural members of the sample population) to a portion of the stimulus or presentation. The audience can be exposed to the stimulus or presentation over a period of time or through a sequence of steps or events. The period of exposure can be divided into windows or portions or events that correspond to elements or events that make up the stimulus or presentation. For example, the synchrony of the response can be determined as a function of the rate of change of a biologically based response to a portion of the stimulus or an event during the presentation by a plurality of audience members or the population sample.

In accordance with the invention, the input to the data processor 16 can be an N by M data matrix where N is the number of subjects and M is the number of time points during which the biological response is recorded. The data processor 16 can include a synchrony processing module which receives the N by M matrix of biological response data, calculates an inverse variance across the matrix values and determines one or more standardized scores for each biological response measured and each time slot. The output will be a total integer score of the synchrony of response across subjects in time windows of W seconds width (this is a variable parameter that depends on the stimulus). In accordance with the invention, the synchrony of a given response is determined by evaluating the rate of change of the response in a given time window or slot over the period of exposure for each participant in the test audience.

The synchrony score can be calculated according to the following steps.

Step 1: Following a noise reduction process for each input channel, create a sliding window of variable width moving forward in time increments that are smaller than the window size.

Step 2: In each window, for each participant, compute the first derivative of one or more of the response endpoints.

Step 3: Across all participants, calculate the mean ($\mu$) and the standard deviation ($\sigma$) of the rate of change in each window.

Step 4: From the above compute a score=$-\ln|\sigma-\mu|$.

Step 5: Scale the resultant score so that all numbers are between 0 and 100.

Step 6: Compute the windowed scores commensurate with the intensity score windows by averaging the sliding scores into sequential windows of variable length time-locked to the media stimulus. The score thus created is the synchrony score per unit time or per time slot.

Additional methods of determining synchrony score are disclosed in U.S. patent application Ser. No. 12/426,259, which is hereby incorporated by reference in its entirety.

Engagement Score

The intensity and synchrony scores may be added together to compute the moment-to-moment engagement score per unit time or per time slot. Depending on the nature of the test presentation and the test audience, one of the intensity and synchrony scores may be weighted relative to other. For example, for some tests it may be preferred to identify the most extreme responses and thus intensity would be weighted more heavily. Alternatively, different functions can be used to determine different forms of the engagement score. For example, multiplying intensity by synchrony creates exaggerated graphs more readable and usable in some situations such as when evaluating multiple hours of trial testimony, it may be useful to identify the most extreme examples of engagement.

Figure 4B:
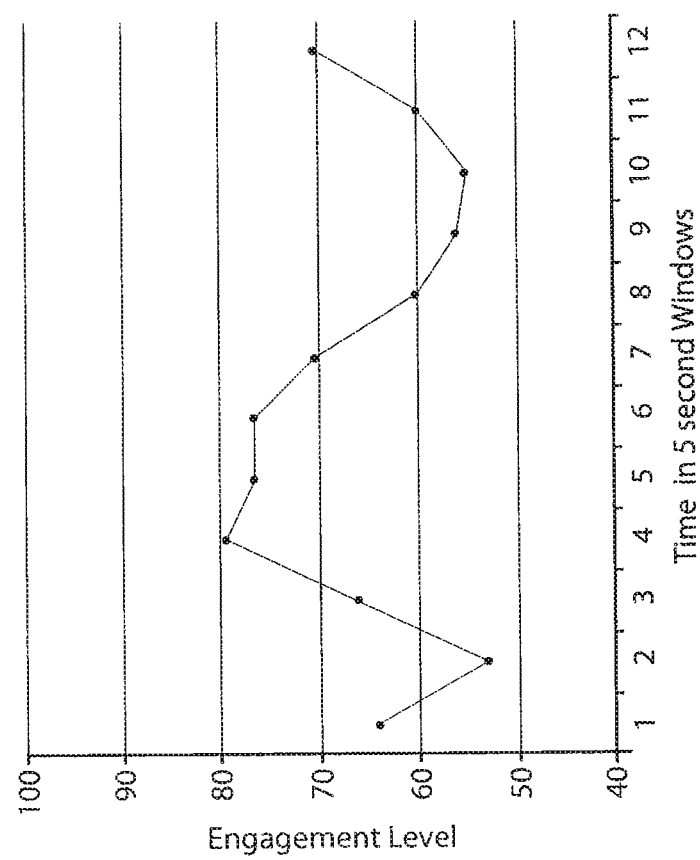

FIGS. 4A and 4B show two examples of a measure of engagement determined in accordance with the invention. The diagrams were generated from a sample population audience of 20 males. FIG. 4A shows a measure or pattern of engagement for a 30 second commercial, the time period is divided into six 5 second time slots and an engagement value from 40 to 100 is determined for each time slot. As the diagram in FIG. 4A shows, the pattern of engagement increases with time. FIG. 4B shows a measure or pattern of engagement for a 60 second commercial, the time period is divided into twelve 5 second time slots and an engagement value from 40 to 100 is determined for each time slot. The commercial of FIG. 4A had three times the number of viewers who did not change the channel as compared to the commercial of FIG. 4B.

Derived Engagement Metrics

As discussed above, a measure of engagement (engagement score) of a content stimulus (show segment, commercial, presentation, and/or similar media) may be obtained by collecting and analyzing the physiological signals of a test group while watching the content stimulus. In addition, many engagement metrics may be derived from the engagement score over the duration of the content.

The derived metrics may include, but are not limited to, average engagement, maximum engagement, negative buildup, and positive buildup. The average engagement is defined as the sum of the engagement scores for each time interval divided by the number of time intervals. The maximum engagement score is defined as the highest engagement score over the entire duration of the content.

The negative buildup is defined as the area of the engagement curve below a specific threshold value and is calculated by 1) dividing the engagement curve into "descending" time intervals (where the engagement score stays constant or decreases between time intervals), 2) computing the area for each descending time interval below the threshold value, 3) summing the areas, and 4) dividing the sum by the overall duration of the content. Segments are considered to contribute to the descending segment if the engagement value rises less than 25% of the total decline of the descending segment.

According to one aspect of the invention, the threshold value for the negative engagement is at most about 60. In one embodiment, the threshold value for the negative engagement is set to an engagement score of about 55. In another embodiment, the threshold value for the negative engagement is set to an engagement score of about 50 or less.

The positive buildup is defined as the area of the engagement curve above a specified threshold value and is calculated by (1) dividing the curve into "ascending" segments (where the engagement value remains or increases between successive time intervals), and (2) computing the area (above the specified threshold) for each such ascending curve, (3) summing all such areas, and 4) dividing the sum by the duration of the content to derive the positive engagement buildup for the content stimulus. Segments are considered to contribute to the ascending segment if the engagement value descends less than 25% of the total rise of the ascending segment.

According to one embodiment, the threshold value for the positive engagement is set to an engagement score of about 50 or more. In another embodiment, the threshold value for the positive engagement is set to an engagement score of about 60. In another embodiment, the threshold value for the positive engagement is set to an engagement score of about 65.

When the goal is to predict whether an audience member is likely to watch an entire presentation of live (non-recorded) content, the preferred metrics include, but are not limited to: positive buildup, average engagement score, and maximum engagement. When assessing whether an audience or member of the audience is likely to fast-forward through recorded content, the preferred metrics include, but are not limited to: negative buildup, average engagement score, and maximum engagement. However, any of the metrics may be used to predict an audience member's behavior.

In one embodiment, the positive buildup is used to predict the likelihood that an audience member will be motivated to watch the entirety of the content stimulus. In addition, a high positive buildup is associated with the likelihood that the audience member will watch the content again in other media forms. For example, a commercial with a high positive buildup shown during a televised sporting event may also be likely to be seen or discussed in another media forms such as on a website or other social media.

In another embodiment, the maximum engagement score is utilized to determine the success of a particular content stimulus. For example, a commercial with a high maximum engagement score generally has a lower likelihood of being fast-forwarded or disregarded than a commercial with a lower maximum engagement score. Armed with the maximum engagement score, an advertiser may rank the potential success of a commercial before it is aired. In addition, a high maximum engagement score is indicative of content that has an impactful individual moment, which may be used for branding purposes.

According to one aspect of the invention, the negative buildup is used to predict the likelihood that an audience member will fast-forward through the content stimulus. For example, a commercial with a high negative buildup is more likely to be fast forwarded when an audience member is watching recorded content than a commercial with a low negative buildup. This information is useful when determining the order of commercials to be played during a program. Placing a first commercial with a high negative buildup before a second commercial with a low negative buildup would be detrimental to the second commercial's viewership because the audience member would likely fast forward through the first and second commercials.

In another embodiment, the average engagement may be used to rank content stimulus. For example, a commercial with a high average engagement may be ranked higher than a commercial with a low average engagement. In addition, a high average engagement may be associated with a decreased likelihood that an audience member will fast-forward or disregard the content.

In one embodiment, one or more of the engagement metrics are compared to a database of engagement metrics and ranked accordingly. For example, the maximum engagement for a commercial can be compared to a database of maximum engagement scores to determine the relative strength of the commercial. In one embodiment, the maximum engagement is given a percentile ranking based on a database of maximum engagement scores. Although maximum engagement is discussed, any of the engagement metrics may be used to determine the relative strength of the content stimulus.

In another embodiment, a plurality of content stimuli are presented and ranked in order by the value of one or more engagement metrics. For example, three commercials may be presented to an audience. Once the engagement metrics for each commercial are calculated as described above, the commercials may be ranked in order of the values for a specific engagement metric. The commercial with the highest maximum engagement is ranked first, and the lowest maximum engagement is ranked third. Although maximum engagement is discussed, any of the engagement metrics may be used to determine the relative strength of the content stimulus.

Comparison to Known Viewership Retention Numbers

The metrics described above may be compared with available viewer data from a data collection service. There are many sources of data relating to viewing statistics for both live and recorded viewership. For example, TiVo™ offers a ratings service called StopWatch™, which provides viewing statistics for a random sample of 100,000 subscribers.

Once obtained, the metrics can be compared against known viewership numbers to determine the degree of correlation. For example, using viewership retention numbers from a commercial source, such as Tivo™, the engagement metrics can be correlated to the viewership retention data. The viewership retention data is only useful for determining that an audience member fast-forwarded or otherwise disregarded the content. However, from the engagement metrics, a determination can be made as to what caused the user to disregard the content. In other words, the engagement metrics help to determine the why the audience behavior occurred.

Figure 7:
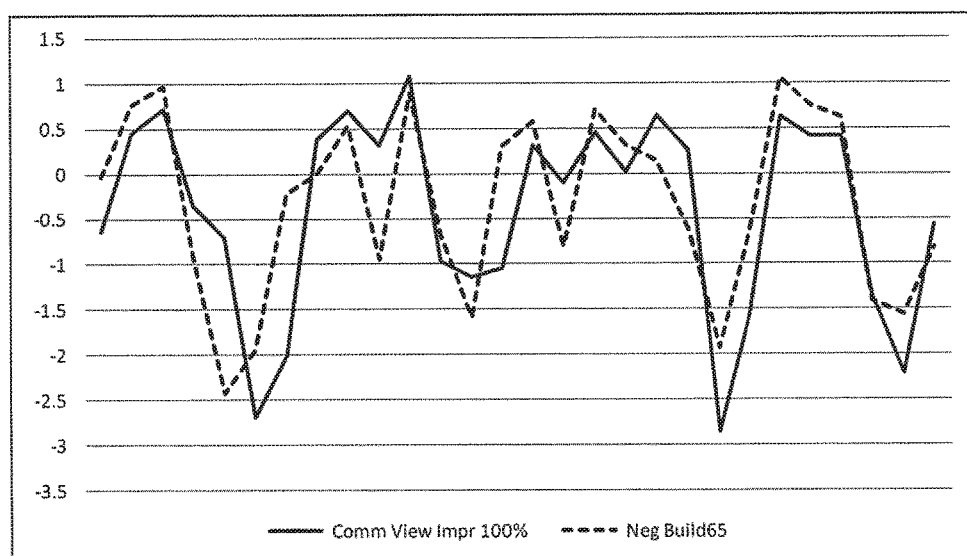
FIG. 7 shows the correlation between negative buildup and commercially obtainable viewership retention data.
Figure 8:
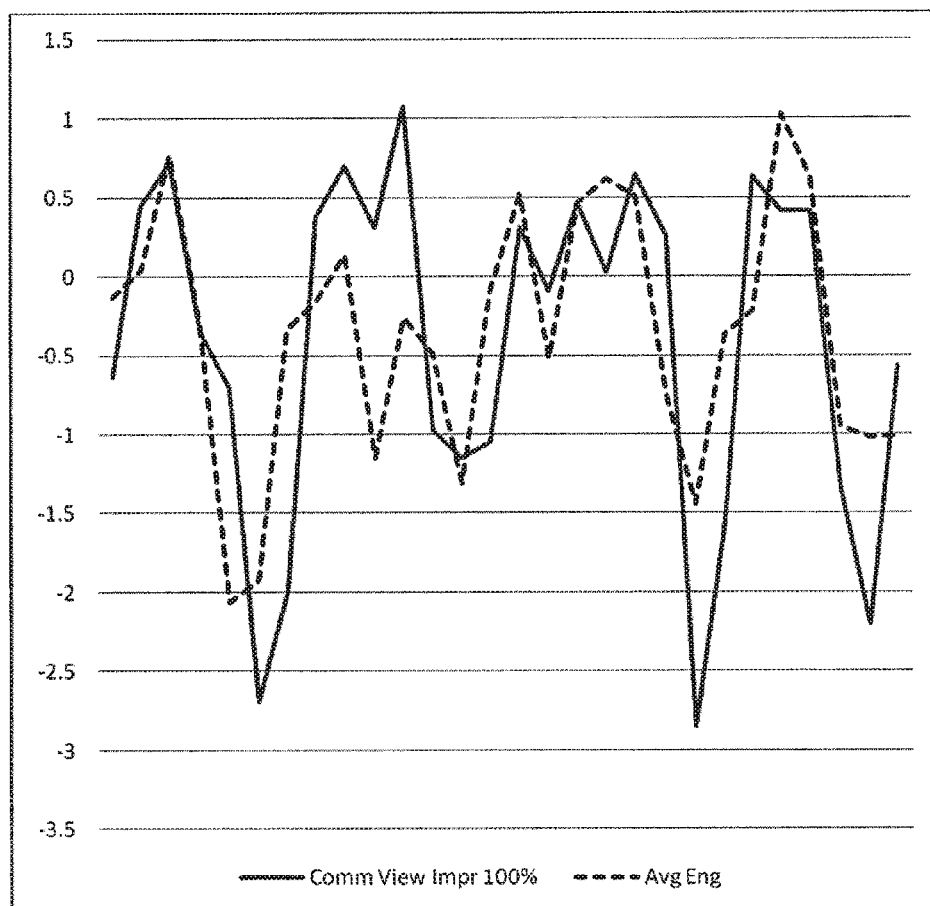
FIG. 8 shows the correlation between average engagement and commercially obtainable viewership retention data.
Figure 9:
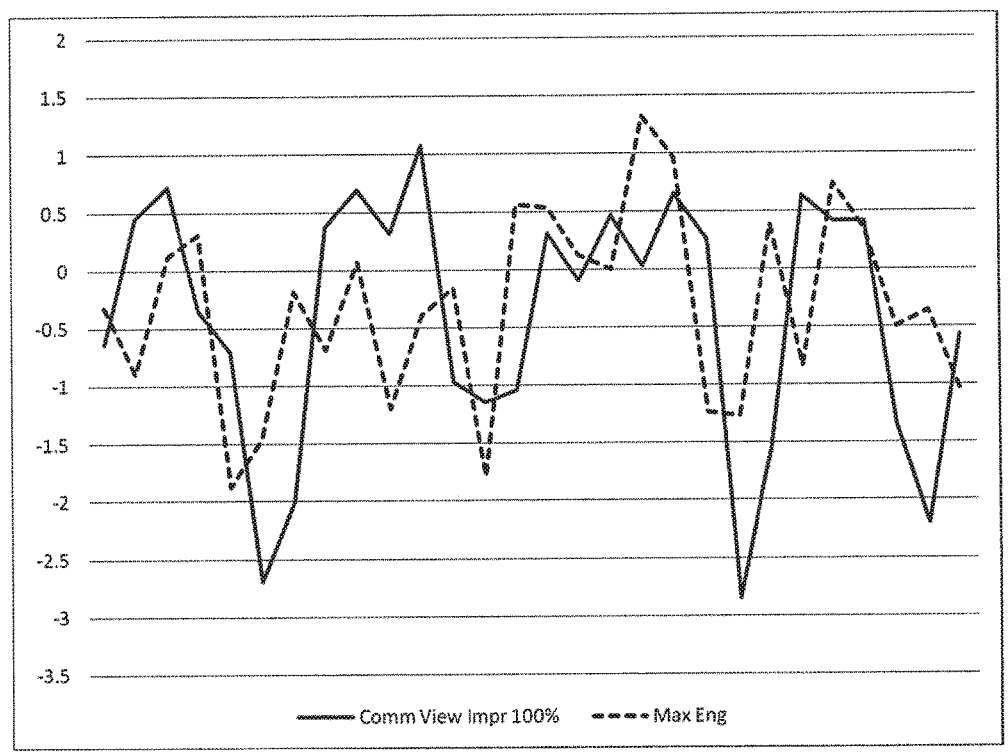
FIG. 9 shows the correlation between maximum engagement and commercially obtainable viewership retention data.

The correlations between viewership retention and average engagement, maximum engagement, and negative buildup are effective in predicting the likelihood of a viewer watching the entire content after watching a minimum of three seconds of the commercial or show segment. As shown in FIGS. 7-9, the engagement metrics are closely correlated to the known retention numbers for various points in a televised program.

For example, FIG. 7 shows the correlation between normalized negative buildup and the viewership retention data obtained from a commercial source. FIG. 8 demonstrates the close correlation between average engagement and viewership retention data. FIG. 9 shows the correlation between the maximum engagement and the viewership retention data.

Predictive Modeling

The system can further include a database of audience engagement to a variety of historic media or other relevant stimuli or experiences that when combined with demographic/psychographic profiles and other data relevant to the test content that allows for a prediction of the relative success of that content in a similar population. After testing an audience, various forms of the output from the described method can be used to estimate the likelihood of the success of the sensory stimulus in achieving its goal. The statistical analyses for creating predictive models can include, but are not limited to, variables related to the product or the content itself, the price of sale or cost of production of the product or content, the place of purchase or medium of experience, the cost of promotion, and/or the characteristics of the audience. For example, factors included in a model for the television industry may include but are not limited to: a) number of viewers per time slot, b) ratings of the lead-in show, c) ratings of the following show, d) mean ratings for the type of show, e) lead actor/actress popularity rating, f) time of year, g) advertising revenue, h) promotional budget for the show, and/or i) popularity of the network. Other factors may include but are not limited to characteristics of the target audience such as: a) reported liking of the show, b) psychographic characteristics (e.g., introversion vs. extroversion), c) demographic characteristics, and/or d) ability to recall or recognize elements of the show. Indicators of success can include but are not limited to how likely a population with similar characteristics is to watch the television show outside of a testing theater and/or how likely a population with similar characteristics will remember and/or purchase the products being advertised. Preferably, the more people tested (the larger the sample population) and the better characterized the population, the more likely that the model can be an accurate predictor of a larger population response. The preferred predictor model can include, but is not limited to, any of the following statistical methods: a) mixed media models, b) traditional multivariate analyses, c) hierarchical linear modeling, d) machine learning, e) regression analyses, f) Bayesian shrinkage estimators, and/or g) cluster and factor analyses.

Figure 2A:
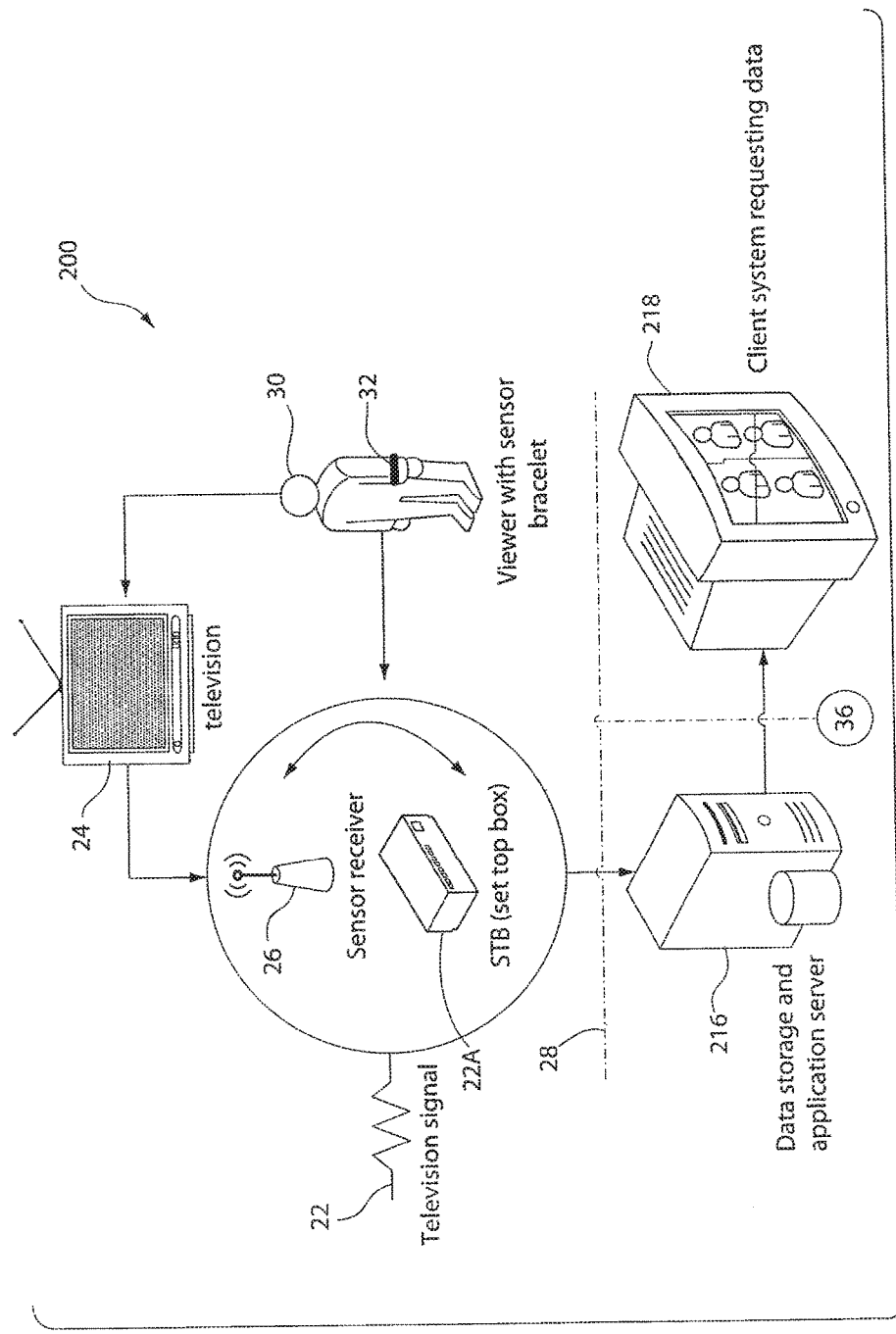
FIG. 2A is a schematic diagram of a second embodiment of the system according to the invention for audience measurement in the home.

FIG. 2A shows a schematic diagram 200 of a second embodiment of the system according to the invention. In this embodiment, the media stimulus is presented via commercially available video signals 22, such as the cable TV signal and plugs into the STB 22A. In turn, the STB 22A enables programs to be displayed on the media device 24 such as a TV monitor, computer, stereo, etc. In this system, a participant 30 in viewing distance wearing a wireless biological sensor package in an unobtrusive form factor like a bracelet 32 interacts with the media device. As long as that person is in basic viewing distance, the sensor receiver 26, which can be a separate unit or built into the STB 22, will receive information about that participant. The system 200 can time-stamp the biological responses along with the unique identifier of that participant. This data can be time-stamped against the programming currently being played by the participant. This information can be sent back to a central database 216 via a transmission network 28 such as an internet connection, pager, or cellular network. The data can be combined with demographic, household, family, community, location and any other type of information potentially relevant to the end-user and processed by software using the scoring algorithm described in this application to calculate the moment-to-moment pattern of engagement and compared to a database of other audience responses to the same or similar media test stimulus 36 and processed using the engagement score and/or predictive models as described above and delivered to a user-interface (11) to generate reports for distribution.

Figure 2B:
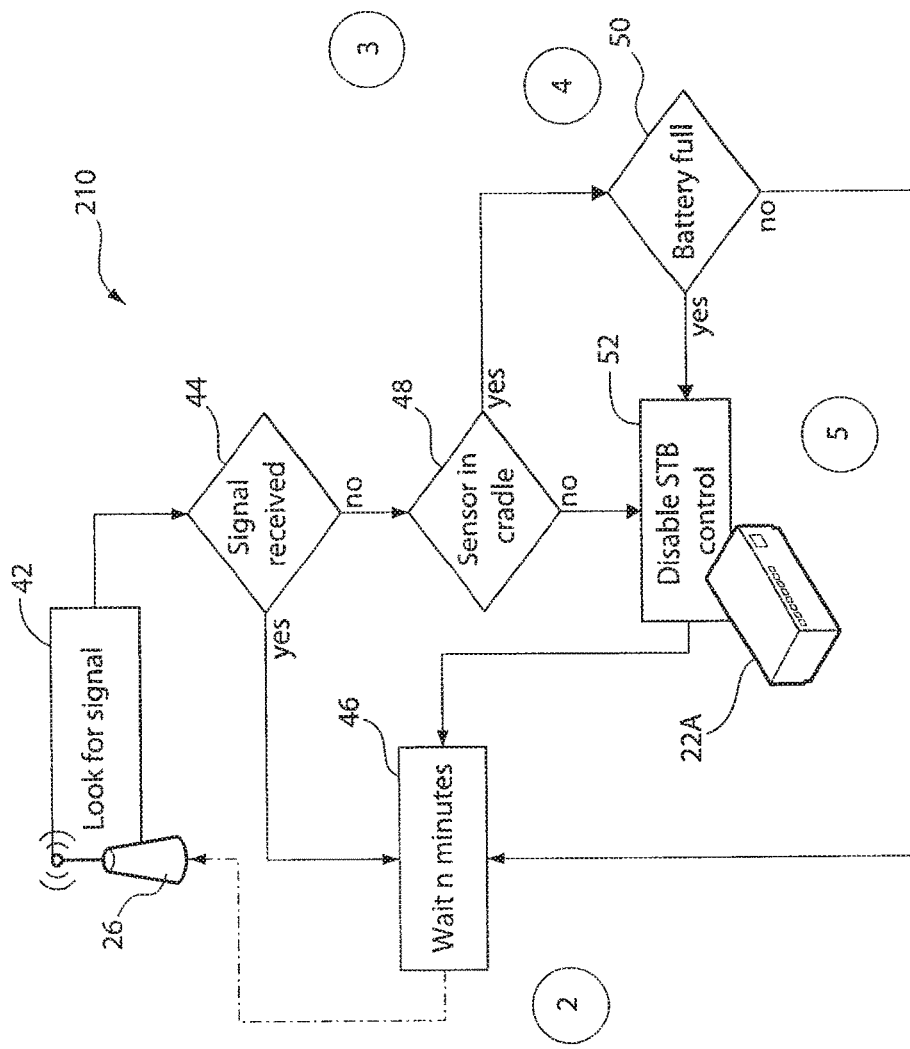
FIG. 2B is a flow diagram of the in-home compliance algorithm for the second embodiment.

FIG. 2B shows a flow diagram 210 of the in-home compliance algorithm to improve usage of the in-home embodiment of this invention. In a household where this system can be set up, compliance can be dealt with by controlling the ability to change programming on the media device being used. The STB 22A can be programmed such that it will not function (partially or completely) if the sensor device is not being worn and is not active. If the sensors are being worn or charging, the STB can be programmed to work. If, however, the sensors are not being worn and are fully charged, the STB can be programmed not to respond fully or partially. In a partial functionality mode, only certain stations may be available, for example, public access and emergency stations. The flow chart 210 of the operation involves a receiver 26 that checks 44 to see if it is getting a signal 42 from the sensor or sensors, which is only possible if the sensor is activated and is being worn. If the receiver is getting a signal, it waits a set amount of time before starting over 46. If it does not receive a signal, the system checks whether a sensor device is being charged in the attached cradle 48. If so and the battery is not full, it also waits a set interval before checking again 50. If, however, the sensor is not active, not charging or fully charged and not being used, the STB can become inactive until the next check shows a change 52.

Figure 2C:
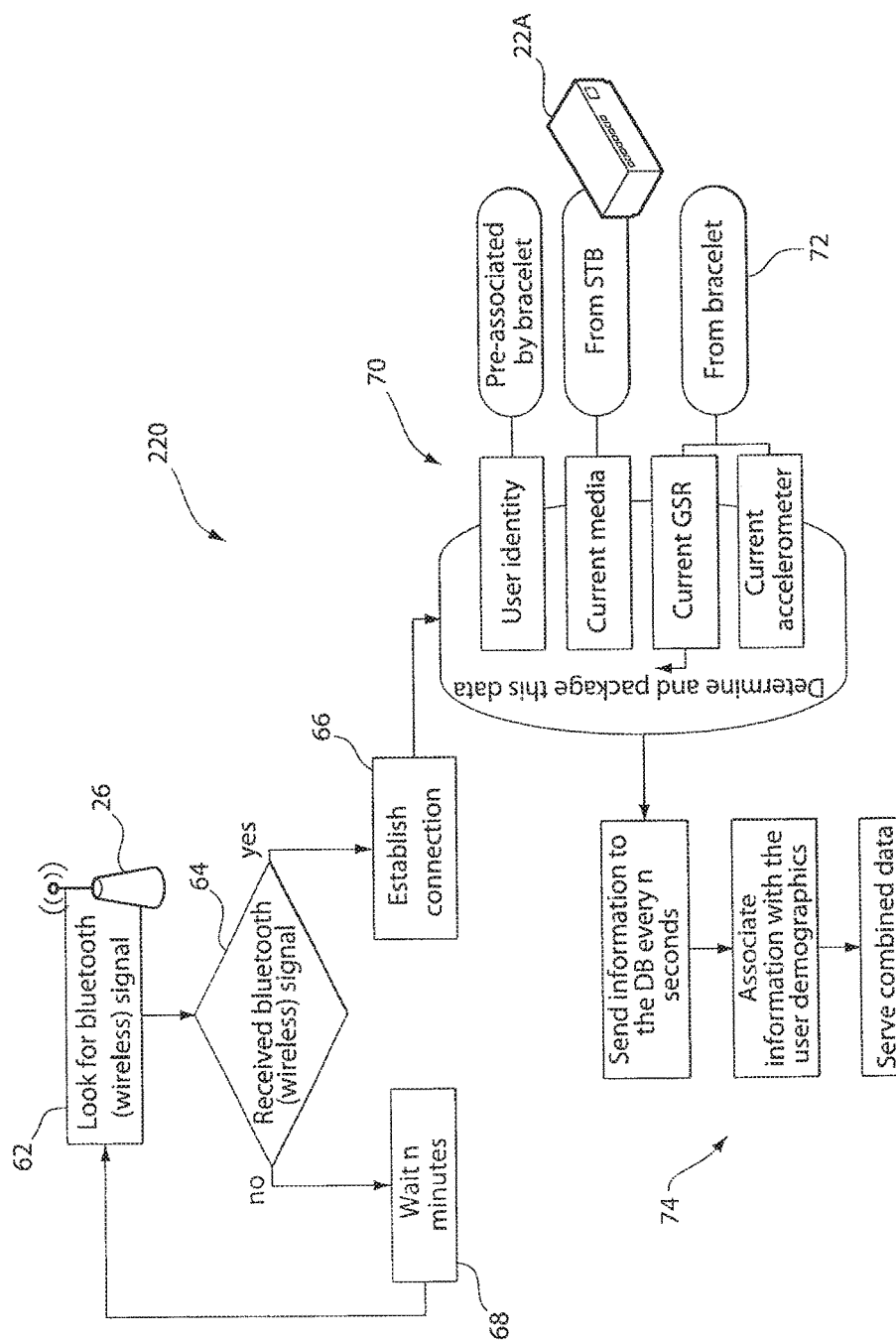
FIG. 2C is a flow diagram of one aspect of the in-home system, its ability to identify who in a given household is actually experiencing media.

FIG. 2C shows one aspect of the in-home system, i.e., its ability to identify who in a given household is actually watching. The wireless technology involved in connecting the sensor with the receiver sends out a unique identifier. This identifier will be related to the data sent out in order to identify the source of the biometric data and link it to the current media stimulus. Anyone wearing a sensor but not in the defined wireless range from the receiver will not have their information tracked while outside of that range. The system will wait for a period time 68 if no wireless signal is received. If they are in the range of another receiver 62 (and STB 26) and the signal is received 62, however, their information can be tracked by that system. The flow chart 220 involves a wireless technology 26 (e.g., Bluetooth) that is used to connect the sensor device to the receiver or STB 22A. Wireless communications can be used to establish a connection 66 and transfer data between the receiver (not shown) and the STB 22A as well as to transfer data needed to determine compliance above. Once a participant is identified, information regarding that participant is collected and sent 70 to the database (DB) and processed as above 74 to generate reports for distribution.

Figure 3:
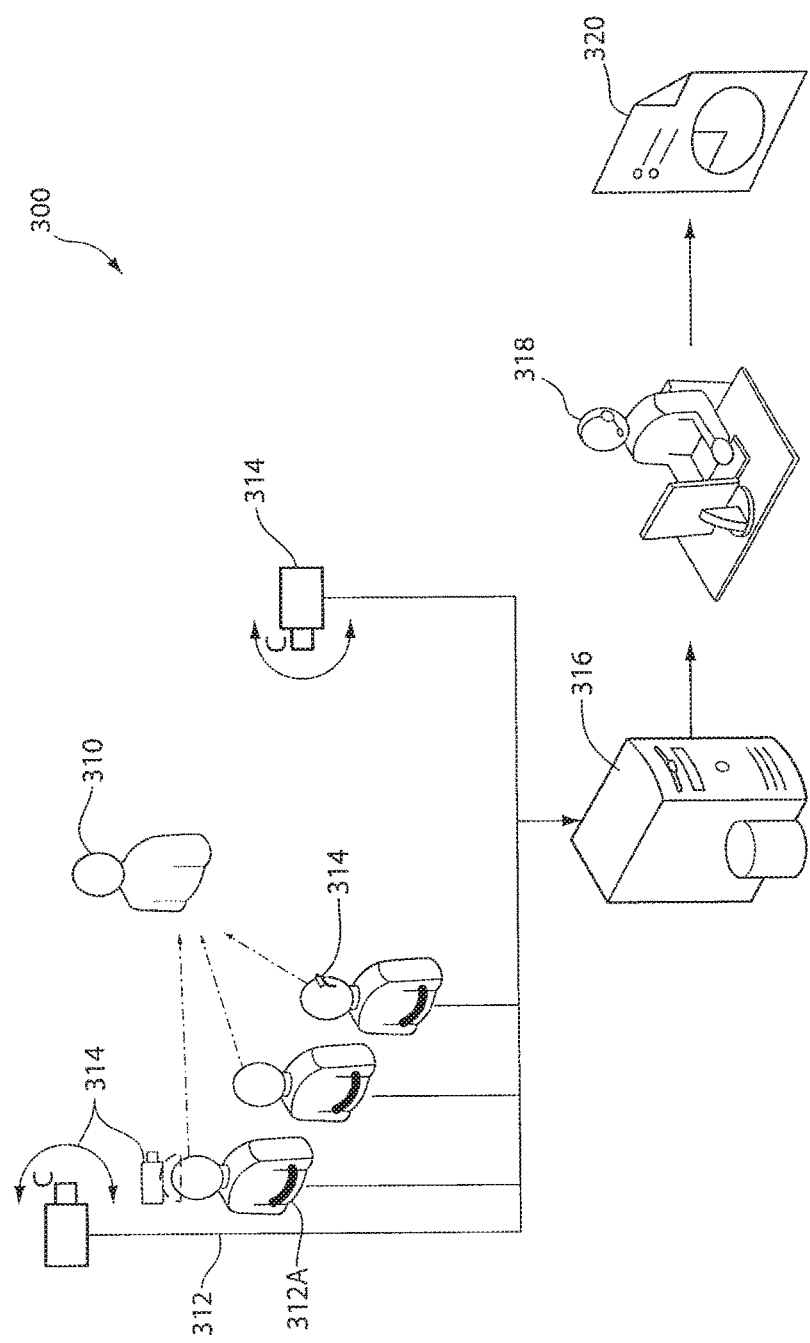
FIG. 3 is a schematic diagram of the third embodiment of the system according to the invention for monitoring levels of engagement during social interaction.

FIG. 3 shows a schematic diagram of the third embodiment of the system 300 according to the invention. In this embodiment, the sensory stimulus can be a live person 310 and the system and method of the invention can be applied to a social interaction that can include, but is not limited to live focus group interactions, live presentations to a jury during a pre-trial or mock-trial, an interview-interviewee interaction, a teacher to a student or group of students, a patient-doctor interaction, a dating interaction or some other social interaction. The social interaction can be monitored for each individual 312 participants biologically based responses time-locked to each other using a biological monitoring system 312A. An optional audio-video camera or other monitoring device can be focused on the audience 314 to monitor facial responses and/or eye-tracking fixation duration and location. The data-sources can be time-locked to each other and sent to a computer data processing device 316. The data processing device 316 can run software that includes the scoring algorithm to calculate the moment-to-moment pattern of engagement and compare it to a database of other audience responses to the same or similar media test stimulus and deliver the results to a user-interface 318. The results can be processed in a predictor model as described above and interpreted and collected into a report 320 for distribution.

The algorithm can be either presented alone or plugged into a model of the relevant industry. Taking television pilot testing as an example, the model can include factors such as:
1. Typical viewers per timeslot
2. The ratings of the lead-in show
3. The ratings of the following show
4. Average ratings per genre
5. Actor popularity—QRating
6. Ratings of shows competing in the timeslot
7. Time of year
8. Promotional budget for the show
9. Demographics of the network An example from advertising can include all of these variables but may add:

1. Flighting/repetition
2. Length of segment
3. Audience target
4. Demographics of the containing program

EXAMPLES

The following non-limiting examples are merely illustrative of the preferred embodiments of the present invention, and are not to be construed as limiting the invention, the scope of which is defined by the appended claims.

Example 1

Engagement metrics are obtained by measuring biologically-based signals. In particular, once the intensity and synchrony scores are obtained as discussed above, the engagement score is obtained in 5-second intervals. The engagement score is averaged over the entire content, minus the first 5-second interval to account for context effects, to obtain the average engagement. The maximum engagement is obtained by reviewing the engagement scores over the entire duration of the content and ascertaining the highest level of engagement, excluding the first 5-second interval to account for context effects.

Figure 5:
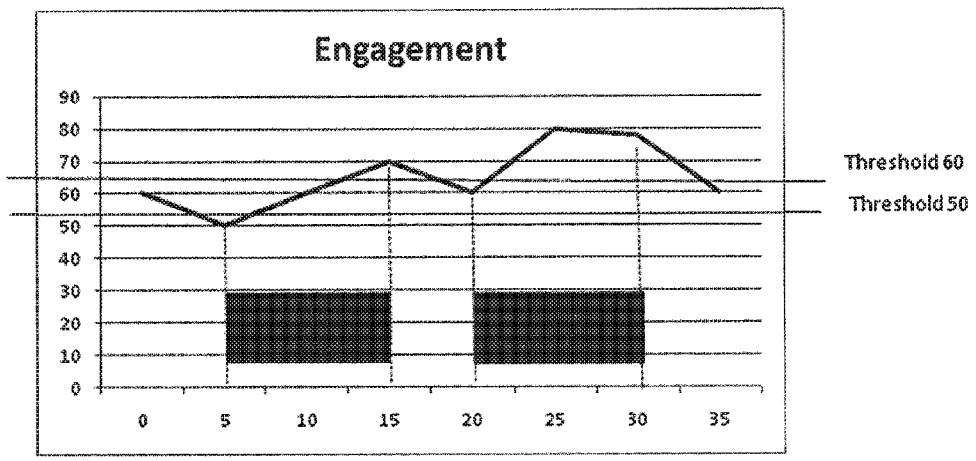
FIG. 5 shows an engagement pattern for a 35 second commercial according to the invention.

FIG. 5 shows an engagement curve or engagement pattern for a 35 second content stimulus. In this case, the content stimulus is a commercial. The X-axis represents time in seconds, and the Y-axis represents the engagement score.

A threshold value of 50 is used for the purposes of this example. The positive buildup is calculated by identifying ascending segments. As shown in FIG. 5, the first ascending segment is from 5 s to 15 s. The engagement at 20 s drops well below the peak at 15 s, which excludes the segment from 15 s to 20 s as an ascending segment. The second ascending segment is from 20 to 30 s. In this example, the 30 s value is lower than that at 25 s; however, the drop in engagement score of (80−78)=2 is less than 25% of the total rise in the segment (80−60), which is 0.25*20=5 pts. Thus, the point "78" is considered a part of the ascending segment. However, the area above the descending portion of the segment (from 25 s to 30 s) and below the maximum (80) of the segment will be subtracted from the total.

Next, the areas above the threshold value of 50 for the ascending segments are calculated. The area in ascending segment 1=(70−50)*(15−5)/2=100. The area of ascending segment 2=(80−60)*(25−20)/2+(80−60)*(30−25)−(80−78)*(30−25)/2+10=245. Then, the ascending segment areas are summed as follows: 100+245=345. Finally, the summed total is divided by the duration of the content to calculate the positive build up above the threshold value of 50 as 345/35=9.86.

To compute positive buildup above threshold 60, only the areas above 60 would be determined. The areas will then be modified as follows:

Area in ascending segment 1=(70−60)*5/2=25

Area in ascending segment 2=(80−60)*(25−20)/2+(80−60)*(30−25)−(80−78)*(30−25)/2=145.

Thus, the positive buildup above a threshold value of 60=(145+25)/35=4.86

Example 2

Figure 6:
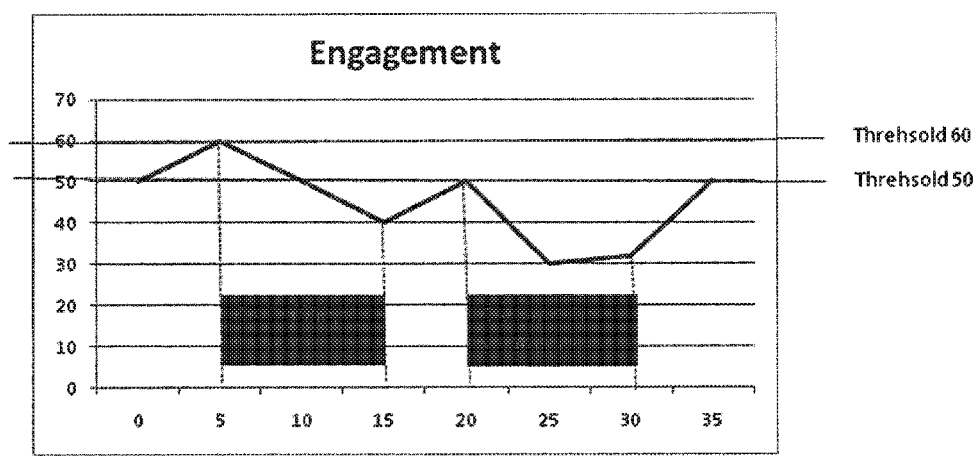
FIG. 6 shows an engagement pattern for a 35 second commercial according to the invention.

FIG. 6 shows the engagement curve or engagement pattern for a 35 s commercial. As in FIG. 5, the X-axis represents time in seconds, and the Y-axis represents the engagement values for commercial.

The negative buildup is computed as described above. First, the descending segments are identified. As shown in FIG. 6, the descending segments are from 5 s to 15 s, and from 20 seconds to 30 seconds. In this example, the 30 s value is higher than that at 25 s; however, the rise in engagement score of (32−30)=2 is less than 25% of the total decline in the segment (50−30), which is 0.25*20=5 pts. Thus, the point "32" is considered a part of the descending segment. However, the area below the ascending portion of the segment (from 25 s to 30 s) and above the minimum (30) of the segment will be subtracted from the total.

Next, the areas of the descending segments below the threshold value are calculated. For a threshold value of 50, the area of the first segment below the threshold value is: (50−40)*5/2=25. The area below the threshold value for the second segment is: (50−30)*5/2+(50−30)*5−(32−30)*5/2)=145. The areas are added to give 145+25=170. As shown in FIG. 6, there is a slight rise from 25 s to 30 s. Finally, the sum is divided by the total duration of the content to give the negative buildup below 50 as: 170/35=4.86.

Following the same procedure, the negative buildup for a threshold value of 60 is and is calculated as follows: The area for below the threshold value for the first segment is (60−40)*10/2=100. The area below the threshold value for the second segment is: (50−30)*5/2+(60−50)*5+(60−30)*5−(32−30)*5/2)=245. The areas are added to give 245+100=345. Finally, the sum is divided by the total duration to calculate the negative build up as: 345/35=9.86.

Other embodiments are within the scope and spirit of the invention. For example, due to the nature of the scoring algorithm, functions described above can be implemented and/or automated using software, hardware, firmware, hard-wiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An apparatus comprising:
    a biometric sensor to measure a biometric response of an audience member during presentation of media on a media device, the media device controllable by the audience member to change the presentation to other media;
    a control device to:
        receive signals indicative of the biometric response from the biometric sensor when worn by the audience member; and
        determine, based on the signals received from the biometric sensor, whether the audience member is wearing the biometric sensor, the control device to:
            if the biometric sensor is not being worn by the audience member, disable an ability to change the presentation on the media device to the other media; and
            if the biometric sensor is being worn by the audience member, transmit the signals indicative of the biometric response;
    an engagement processor to receive the signals indicative of the biometric response, the engagement processor to:
        generate an engagement curve for the audience member based on the biometric response;
        identify an interval of the engagement curve having ascending engagement;
        determine an area above a threshold value and below the engagement curve for the interval; and
        determine a positive buildup value for the media based on a ratio of the area to a duration of the media; and
    a prediction processor to predict viewership based on the positive buildup value and generate for display or output information indicating a prediction of the viewership.

2. The apparatus of claim 1, wherein the interval of the engagement curve includes an ascending engagement portion and a descending engagement portion.

3. The apparatus of claim 2, wherein the engagement processor is to:
    determine whether a decrease in engagement during the descending engagement portion is less than a threshold percentage of an increase in engagement during the ascending engagement portion.

4. The apparatus of claim 3, wherein the engagement processor is to:
    identify the interval as having the ascending engagement portion if the decrease in engagement is less than the threshold percentage of the increase in engagement.

5. The apparatus of claim 1, wherein the prediction processor is to rank the media based on a comparison of the positive buildup value to other positive buildup values of other media.

6. The apparatus of claim 1, wherein the prediction processor is to determine a likelihood that the audience member will watch the media again in another form.

7. The apparatus of claim 1, wherein the prediction processor is to determine a percentile rank for the positive buildup value based on a database of positive buildup values.

8. The apparatus of claim 1, wherein the prediction processor is to predict the viewership based on the positive buildup value by determining whether a viewer will watch the entirety of the media when the media is live.

9. The apparatus of claim 1 further including:
    an intensity processor to determine, based on the biometric response, intensity scores for the audience member; and
    a synchrony processor to determine synchrony scores based on the biometric response and a biometric response of another audience member, the engagement processor to generate the engagement curve based on the intensity scores and the synchrony scores.

10. An apparatus comprising:
    a biometric sensor to measure a biometric response of an audience member during presentation of media on a media device, the media device controllable by the audience member to change the presentation to other media;
    a control device to:
        receive signals indicative of the biometric response from the biometric sensor when worn by the audience member; and
        determine, based on the signals received from the biometric sensor, whether the audience member is wearing the biometric sensor, the control device to:
            if the biometric sensor is not being worn by the audience member, disable an ability to change the presentation on the media device to the other media; and
            if the biometric sensor is being worn by the audience member, transmit the signals indicative of the biometric response;
    an engagement processor to receive the signals indicative of the biometric response, the engagement processor to:

generate an engagement curve for the audience member based on the biometric response;
identify an interval of the engagement curve having descending engagement;
determine an area below a threshold value and above the engagement curve for the interval; and
determine a negative buildup value for the media based on a ratio of the area to a duration of the media; and
a prediction processor to predict viewership based on the negative buildup value and generate for display or output information indicating a prediction of the viewership.

11. The apparatus of claim 10, wherein the interval of the engagement curve includes a descending engagement portion and an ascending engagement portion.

12. The apparatus of claim 11, wherein the engagement processor is to:
determine whether an increase in engagement during the ascending engagement portion is less than a threshold percentage of a decrease in engagement during the descending engagement portion.

13. The apparatus of claim 12, wherein the engagement processor is to:
identify the interval as having the descending engagement portion if the increase in engagement is less than the threshold percentage of the decrease in engagement.

14. The apparatus of claim 10, wherein the prediction processor is to rank the media based on a comparison of the negative buildup value to other negative buildup values of other media.

15. The apparatus of claim 10, wherein the prediction processor is to determine whether a viewer will watch the entirety of the media when the media is previously recorded.

16. The apparatus of claim 15, wherein the prediction processor is to determine whether the viewer will watch the entirety of the media by determining a likelihood that the viewer will fast-forward through the media.

17. The apparatus of claim 10, wherein the prediction processor is to determine an order to present the media in relation to other media based on the negative buildup value.

18. The apparatus of claim 10, wherein the prediction processor is to determine a percentile rank for the negative buildup value based on a database of negative buildup values.

19. The apparatus of claim 10 further including:
an intensity processor to determine, based on the biometric response, intensity scores for the audience member; and
a synchrony processor to determine synchrony scores based on the biometric response and a biometric response of another audience member, the engagement processor to generate the engagement curve based on the intensity scores and the synchrony scores.

* * * * *